(12) United States Patent
Johnson et al.

(10) Patent No.: US 11,415,546 B2
(45) Date of Patent: Aug. 16, 2022

(54) VOLATILE ORGANIC COMPOUND-BASED DIAGNOSTIC SYSTEMS AND METHODS

(71) Applicants: The Trustees of The University of Pennsylvania, Philadelphia, PA (US); Monell Chemical Senses Center, Philadelphia, PA (US)

(72) Inventors: Alan T. Johnson, Philadelphia, PA (US); Nicholas J. Kybert, Haverford, PA (US); George Preti, Horsham, PA (US); Katharine A. Prigge, Philadelphia, PA (US); Janos L. Tanyi, Philadelphia, PA (US); Cynthia Otto, Folsom, PA (US)

(73) Assignees: The Trustees of the University of Pennsylvania, Philadelphia, PA (US); Monell Chemical Senses Center, Philadelphia, PA (US)

( * ) Notice: Subject to any disclaimer, the term of this patent is extended or adjusted under 35 U.S.C. 154(b) by 0 days.

(21) Appl. No.: 15/501,338

(22) PCT Filed: Sep. 3, 2015

(86) PCT No.: PCT/US2015/048343
§ 371 (c)(1),
(2) Date: Feb. 2, 2017

(87) PCT Pub. No.: WO2016/036950
PCT Pub. Date: Mar. 10, 2016

(65) Prior Publication Data
US 2017/0227491 A1 Aug. 10, 2017

Related U.S. Application Data

(60) Provisional application No. 62/046,466, filed on Sep. 5, 2014.

(51) Int. Cl.
*G01N 27/414* (2006.01)
*G01N 33/53* (2006.01)
(Continued)

(52) U.S. Cl.
CPC ..... *G01N 27/4146* (2013.01); *G01N 27/4145* (2013.01); *G01N 33/497* (2013.01);
(Continued)

(58) Field of Classification Search
None
See application file for complete search history.

(56) References Cited

U.S. PATENT DOCUMENTS 4,563,893 A 1/1986 Tanyolac et al.
5,369,028 A 11/1994 Harpold et al.
(Continued)

FOREIGN PATENT DOCUMENTS

WO 2010/014903 A1 2/2010
WO 2012/050646 * 4/2012
(Continued)

OTHER PUBLICATIONS

Goldsmith, B.R. et al., "Biomimetic Chemical Sensors Using Nanoelectronic Readout of Olfactory Receptor Proteins", ACS Nano. Jun. 22, 2011, 5(7), 5408-5416.
(Continued)

*Primary Examiner* — Melanie Brown
(74) *Attorney, Agent, or Firm* — BakerHostetler

(57) ABSTRACT

Provided are devices and methods to detect the presence of volatile organic compounds related to the presence of a disease state in a biological sample. The devices may include a detection moiety such as a polynucleotide in
(Continued)

electronic communication with a semiconductor such as graphene or a carbon nanotube.

20 Claims, 20 Drawing Sheets

Specification includes a Sequence Listing.

(51) Int. Cl.
G01N 33/543 (2006.01)
H01L 51/00 (2006.01)
G01N 33/497 (2006.01)
G01N 33/574 (2006.01)
H01L 51/05 (2006.01)
B82Y 30/00 (2011.01)

(52) U.S. Cl.
CPC ..... G01N 33/5308 (2013.01); G01N 33/5438 (2013.01); G01N 33/54373 (2013.01); G01N 33/57449 (2013.01); H01L 51/0045 (2013.01); H01L 51/0048 (2013.01); H01L 51/0093 (2013.01); H01L 51/0545 (2013.01); H01L 51/0562 (2013.01); B82Y 30/00 (2013.01); G01N 2033/4975 (2013.01); G01N 2800/7028 (2013.01)

(56) References Cited

U.S. PATENT DOCUMENTS

| | | | |
|---|---|---|---|
| 6,493,638 | B1 | 12/2002 | McLean et al. |
| 6,649,403 | B1 | 11/2003 | McDevitt et al. |
| 6,905,655 | B2 | 6/2005 | Gabriel et al. |
| 7,129,554 | B2 | 10/2006 | Lieber et al. |
| 8,716,029 | B1* | 5/2014 | Kim .............. G01N 33/5306 436/501 |
| 2003/0124572 | A1 | 7/2003 | Umek et al. |
| 2004/0007740 | A1 | 1/2004 | Abstreiter et al. |
| 2004/0101851 | A1 | 5/2004 | White et al. |
| 2004/0200734 | A1 | 10/2004 | Co et al. |
| 2005/0051719 | A1* | 3/2005 | Miller ............. G01N 27/622 250/287 |
| 2006/0054936 | A1 | 3/2006 | Lieber et al. |
| 2006/0145194 | A1 | 7/2006 | Barron et al. |
| 2006/0240492 | A1 | 10/2006 | Rusling et al. |
| 2007/0292896 | A1 | 12/2007 | Strano et al. |
| 2008/0008760 | A1 | 1/2008 | Bianco et al. |
| 2008/0063566 | A1* | 3/2008 | Matsumoto ........ G01N 33/5438 422/68.1 |
| 2008/0283875 | A1 | 11/2008 | Mukasa et al. |
| 2009/0053212 | A1 | 2/2009 | Yamamoto et al. |
| 2009/0084678 | A1* | 4/2009 | Joshi ............... A61B 5/14532 204/403.14 |
| 2009/0090175 | A1* | 4/2009 | Shim ................ C12Q 1/6825 73/61.61 |
| 2009/0275066 | A1 | 11/2009 | Popot et al. |
| 2009/0280056 | A1 | 11/2009 | Dennis et al. |
| 2010/0088040 | A1 | 4/2010 | Johnson, Jr. |
| 2010/0105082 | A1 | 4/2010 | Ramadurai et al. |
| 2010/0105834 | A1 | 4/2010 | Tour et al. |
| 2010/0112546 | A1* | 5/2010 | Lieber ............... A61B 5/14546 435/5 |
| 2010/0176837 | A1* | 7/2010 | Kummel .......... G01N 27/4141 324/762.01 |
| 2010/0184669 | A1 | 7/2010 | Harrison et al. |
| 2010/0198521 | A1 | 8/2010 | Haick |
| 2010/0256344 | A1 | 10/2010 | Thompson et al. |
| 2010/0270543 | A1 | 10/2010 | Choi et al. |
| 2011/0059871 | A1 | 3/2011 | Tour et al. |
| 2011/0098591 | A1* | 4/2011 | Haick .............. G01N 33/497 600/532 |
| 2013/0143247 | A1 | 6/2013 | Haick et al. |
| 2014/0015548 | A1* | 1/2014 | Naughton .......... G01R 27/26 324/658 |
| 2014/0155333 | A1 | 6/2014 | Harrison et al. |
| 2015/0119263 | A1 | 4/2015 | Johnson et al. |
| 2016/0077047 | A1* | 3/2016 | Khamis ........... G01N 27/4146 506/3 |

FOREIGN PATENT DOCUMENTS

WO 2012/050646 A2 4/2012
WO 2013/033359 A1 3/2013

OTHER PUBLICATIONS

Furton, K.G. and L.J. Myers, "The scientific foundation and efficacy of the use of canines as chemical detectors for explosives", Talanta, 2001. 54(3): p. 487-500.
Filmore, D., "It's a GPCR World", Modern Drug Discovery, 2004. 7(11): p. 24-28.
Duchamp-Viret, P. et al., "Odor response properties of rat olfactory receptor neurons", Science, 1999. 284(5423): p. 2171-2174.
Denisov, I. G. et al., "Directed self-assembly of monodisperse phospholipid bilayer nanodiscs with controlled size", Journal of the American Chemical Society 2004, 126, (11), 3477-3487.
Dan, Y.P., et al., "Intrinsic Response of Graphene Vapor Sensors", Nano Letters, 2009. 9(4): p. 1472-1475.
D.J. Wasilko and S.E. Lee "TIPS: Titerless Infected-Cells Preservation and Scale-up" (2006), Bioprocessing Journal, 29-32 [Abstract only].
Collins, P.G., et al., "Extreme oxygen sensitivity of electronic properties of carbon nanotubes", Science, 2000. 287(5459): p. 1801-1804.
Christophe, C., et al., "Rats for demining: an overview of the APOPO program", Proceedings of the Eudem Conference on humanitarian landmine detection technologies, 2004.
Chen, R. J. et al., "Noncovalent functionalization of carbon nanotubes for highly specific electronic biosensors", Proceedings of the National Academy of Sciences of the United States of America, 2003, 100, (9), 4984-4989.
Burdo et al., "Osteopontin Prevents Monocyte Recirculation and Apoptosis", J. Leukocyte Bioi., 2007, 81,1504-11.
Breer, H., "Olfactory receptors: molecular basis for recognition and discrimination of odors", Analytical and Bioanalytical Chemistry, 2003. 377(3): p. 427-433.
Bradley, K., et al., "Integration of cell membranes and nanotube transistors", Nano Letters, 2005. 5(5): p. 841-845.
Bayburt, T.H. and S.G. Sligar, "Self-assembly of single integral membrane proteins into soluble nanoscale phospholipid bilayers", Protein Science, 2003. 12(11): p. 2476-2481.
Bayburt, T.H. and S.G. Sligar, "Membrane protein assembly into Nanodiscs", Febs Letters, 2010. 584(9): p. 1721-1727.
Bayburt, T. H. et al., "Self-assembly of discoidal phospholipid bilayer nanoparticles with membrane scaffold proteins", Nano Letters 2002, 2, (8), 853-856.
Bahr, J.L., et al., "Functionalization of carbon nanotubes by electrochemical reduction of aryl diazonium salts: A bucky paper electrode", Journal of the American Chemical Society, 2001. 123(27): p. 6536-6542.
Azpiazu, I. and N. Gautam, "A fluorescence resonance energy transfer-based sensor indicates that receptor access to a G protein is unrestricted in a living mammalian cell", Journal of Biological Chemistry, 2004. 279(26): p. 27709-27718.
Andriole et al, "Mortality Results From A Randomized Prostate-Cancer Screening Trial", N. Engl. J. Med., 2009, 360,1310-9.
Albert, K.J., et al., "Cross-reactive chemical sensor arrays", Chemical Reviews, 2000. 100(7): p. 2595-2626.
Akimov, V., et al., "Nanobiosensors based on individual olfactory receptors", Analog Integrated Circuits and Signal Processing, 2008. 57(3): p. 197-203.
Abaffy, T. et al., "Functional analysis of a mammalian odorant receptor subfamily", Journal of Neurochemistry, 2006, 97, (5), 1506-1518.

(56) References Cited

OTHER PUBLICATIONS

Mahouche-Chergui et al., Aryl diazonium salts: a new class of coupling agents for bonding polymers, biomacromolecules and nanoparticles to surfaces, 2011, Chem. Soc. Rev., vol. 40, pp. 4143-4166.
Lei et al., Nanotubes in Biosensing, Sep./Oct. 2010, Wiley Interdisciplinary Reviews: Nanomedicine and Nanobiotechnology, vol. 2, pp. 496-509.
Zuniga, C., et al., "Nanoenabled microelectromechanical sensor for volatile organic chemical detection", Applied Physics Letters, 2009. 94(22): p. 223122.
Zhou, X.J., et al., "Supported lipid bilayer/carbon nanotube hybrids", Nature Nanotechnology, 2007. 2(3): p. 185-190.
Zhang, Y.B., et al., Functionalized carbon nanotubes for detecting viral proteins. Nano Letters, 2007. 7(10): p. 3086-3091.
Zhang, X. M. et al., "High-throughput microarray detection of olfactory receptor gene expression in the mouse", Proceedings of the National Academy of Sciences of the United States of America 2004, 101, (39), 14168-14173.
Zhang et al., Coding of Sweet, Bitter, and Umami Tastes: Different Receptor Cells Sharing Similar Signaling Pathways, Feb. 7, 2003, Cell 112:293-301.
Zhang et al, "Functionalized Carbon Nanotubes for Detecting Viral Proteins", Nano Lett., 2007, 7(10), 3086-91.
Yoon, H., et al., "Polypyrrole Nanotubes Conjugated with Human Olfactory Receptors: High-Performance Transducers for FET-Type Bioelectronic Noses", Angewandte Chemie—International Edition, 2009. 48(15): p. 2755-2758.
Xu, F.Q., et al., "Simultaneous activation of mouse main and accessory olfactory bulbs by odors or pheromones", Journal of Comparative Neurology, 2005. 489(4): p. 491-500.
Wise, P.M. et al., "Quantification of odor quality", Chemical Senses, 2000. 25(4): p. 429-443.
Wilson, D.A., "Habituation of odor responses in the rat anterior piriform cortex", Journal of Neurophysiology, 1998. 79(3): p. 1425-1440.
Wikipedia.org., "Langmuir equation", http://en.wikipedia.org/wiki/Langmuir eguation, accessed 2014, 5 pages.
White, J., et al., "Solid-state, dye-labeled DNA detects volatile compounds in the vapor phase", Plos Biology, 2008. 6(1): p. 30-36.
Wasilko, D. J. et al., "The titerless infected-cells preservation and scale-up (TIPS) method for large-scale production of NO-sensitive human soluble guanylate cyclase (sGC) from insect cells infected with recombinant baculovirus", Protein Expression and Purification 2009, 65, (2), 122-132.
Uchida, N. and Z.F. Mainen, "Speed and accuracy of olfactory discrimination in the rat", Nature Neuroscience, 2003. 6(11): p. 1224-1229.
Tang, X. et al., "Carbon Nanotube DNA Sensor and Sensing Mechanism", Nano Letters 2006, 6, (8), 1632-1636.
Suwa et al., OR2AG1-Olfactory receptor 2AG1-*Homo sapiens*, Jul. 2001, UniProtKB-C9H205: 12 pages.
Sun, S.J., "Gas adsorption on a single walled carbon nanotube-model simulation", Physics Letters A, 2008. 372(19): p. 3493-3495.
Star, A., et al., Electronic detection of specific protein binding using nanotube FET devices. Nano Letters, 2003. 3(4): p. 459-463.
Staii, C. and AT. Johnson, "DNA-decorated carbon nanotubes for chemical sensing", Nano Letters, 2005. 5(9): p. 1774-1778.
Schwende, F.J. et al., "Volatile Compounds Associated with Estrus in Mouse Urine-Potential Pheromones", Experientia, 1984. 40(2): p. 213-214.
Saito, H. et al., "Odor Coding by a Mammalian Receptor Repertoire", Science Signaling, Nov. 2009, 2, (60), ra9.
Ritchie, T. K. et al., "Reconstitution of Membrane Proteins in Phospholipid Bilayer Nanodiscs", Methods in Enzymology; Liposomes, Pt F, 2009, 464, 211-231.
Repicky, S.E. and C.W. Luetje, "Molecular receptive range variation among mouse odorant receptors for aliphatic carboxylic acids", Journal of Neurochemistry, 2009, 109(1): p. 193-202.
Raming, K., et al., "Cloning and Expression of Odorant Receptors", Nature, 1993, 361(6410): p. 353-356.
Qi et al, "Toward Large Arrays of Multiplex Functionalized Carbon Nanotube Sensors for Highly Sensitive and Selective Molecular Detection", Nano Lett., Mar. 2003, 3(3), 347-51.
Pevsner, J. et al., "Isolation and Characterization of an Olfactory Receptor Protein for Odorant Pyrazines", Proceedings of the National Academy of Sciences of the United States of America, 1985, 82, (9), 3050-3054.
Pengfei, Q.F., et al., "Toward large arrays of multiplex functionalized carbon nanotube sensors for highly sensitive and selective molecular detection", Nano Letters, 2003. 3(3): p. 347-351.
Peng, X.H. et al., "Functional Covalent Chemistry of Carbon Nanotube Surfaces", Advanced Materials, 2009, 21(6), 625-642.
Noy, A. et al., "Bionanoelectronics with 1D materials", Materials Today, 2009. 12(9): p. 22-31.
Nakanishi, S., "Molecular Diversity of Glutamate Receptors and Implications for Brain Function, Oct. 23, 1992, Science 258:597-603.
Misra et al., "Bioelectronic silicon nanowire devices using functional membrane proteins", PNAS, Aug. 18, 2009, 106(33), 13780-13784.
McAlpine, M.C., et al., "Peptide-nanowire hybrid materials for selective sensing of small molecules", Journal of the American Chemical Society, 2008. 130(29): p. 9583-9589.
Lu, Y. et al., "DNA-decorated graphene chemical sensors", Applied Physics Letters, 2010, 97, (8), 083107.
Lerner, M.B. et al, "Hybrids of a Genetically Engineered Antibody and a Carbon Nanotube Transistor for Detection of Prostrate Cancer Biomarkers", ACS Nano., May 10, 2012, 6(6), 5143-5149.
Lee, T.M.H., "Over-the-counter biosensors: Past, present, and future", Sensors, 2008. 8(9): p. 5535-5559.
Kuang, Z.F., et al., "Biomimetic Chemosensor: Designing Peptide Recognition Elements for Surface Functionalization of Carbon Nanotube Field Effect Transistors", Acs Nano, 2010. 4(1): p. 452-458.
Kojima, A., et al., "Protein sensor using carbon nanotube field effect transistor", Japanese Journal of Applied Physics Part 1—Regular Papers Short Notes & Review Papers, 2005. 44(4A): p. 1596-1598.
Kim, T. H. et al., "Single-Carbon-Atomic-Resolution Detection of Odorant Molecules using a Human Olfactory Receptor-based Bioelectronic Nose", Advanced Materials, 2009, 21, (1), 91-94.
Kim, S.N. et al, "Carbon Nanotubes for Electronic and Electrochemical Detection of Biomolecules", Adv. Mater., Oct. 19, 2007, 19(20), 3214-3228.
Khamis et al, "Optimized Photolithographic Fabrication Process for Carbon Nanotube Devices", AIP Advances, 2011, I, 022106.
Khalap, V.R., et al., "Hydrogen Sensing and Sensitivity of Palladium-Decorated Single-Walled Carbon Nanotubes with Defects", Nano Letters, 2010. 10(3): p. 896-901.
Khafizov, K., et al., "Ligand specificity of odorant receptors" Journal of Molecular Modeling, 2007. 13(3): p. 401-409.
Kajiya, K. et al., "Molecular bases of odor discrimination: Reconstitution of olfactory receptors that recognize overlapping sets of odorants", Journal of Neuroscience, 2001, 21, (16), 6018-6025.
International Patent Application No. PCT/US12/53085: International Search Report and Written Opinion dated Jan. 25, 2013, 17 pages.
Huang et al, "Immobilization of Antibodies and Bacterial Binding on Nanodiamond and Carbon Nanotubes for Biosensor Applications", Diamond Relat Mater. , 2004, Apr.-Aug., 3(4-8),I 098-I 02.
Heller et al, "Identifying The Mechanism of Biosensing With Carbon Nanotube Transistors", Nano Lett., Feb. 2008, 8(2), 591-595.
Ha et al. "Printed, Sub-3V Digital Circuits on Plastic From Aqueous Carbon Nanotube luk", ACS Nano Online ASAP, 2010.
Guo, X., et al., "Covalently bridging gaps in single-walled carbon nanotubes with conducting molecules", Science, 2006. 311: p. 356-9.
Graff, R.A., et al., "Synthesis of nickel-nitrilotriacetic acid coupled single-walled carbon nanotubes for directed self-assembly with polyhistidine-tagged proteins", Chemistry of Materials, 2008. 20(5): p. 1824-1829.

(56) References Cited

OTHER PUBLICATIONS

Goldsmith, B.R., et al., "Conductance-controlled point functionalization of single-walled carbon nanotubes", Science, 2007. 315(5808): p. 77-81.
Zheng, M. et al., "DNA-assisted dispersion and separation of carbon nanotubes," Nature Mater., 2003, 2, 338-342.
Zhang, D. et al., "Detection of $NO_2$ down to ppb Levels Using Individual and Multiple $In_2O_3$ Nanwire Devices," Nano Lett., 2004, 4, 1919-1924.
Wong et al., "Covalently Functionalized Nanotubes as Nanometer-Sized Probes in Chemistry and Biology," Nature, 2002, 420, 761.
Williams et al., "Carbon nanotubes with DNA recognition," Nature, 1998, 394, 52-55.
Wang, W. et al., "Label-free detection of small-molecule-protein interactions by using nanowire nanosensors," Proc. Natl Acad Sci. USA, 2005, 102, 3208-3212.
Valentini, L. et al., "Sensors for sub-ppm $NO_2$ gas detection based on carbon nanotube thin films," Appl. Phys. Lett., 2003, 82, 961-963.
Staii, C. et al., "High Frequency Scanning Gate Microscopy and Local Memory Effect of Carbon Nanotube Transistors," Nano Lett., 2005, 5(5), 893-896.
Staii, C. et al., "DNA-Decorated Carbon Nanotubes for Chemical Sensing," Nano Letters, 2005, 5(9), 1774-1778.
Snow, E.S. et al., "Chemical Detection with a Single-Walled Carbon Nanotube Capacitor," Science, 2005, 307, 1942-1945.
Sirdeshmuhk, R. et al., "Biological Functionalization of Carbon Nanotubes," Mat. Res. Soc. Symp. Proc., vol. 823 .COPYRGT. 2004, Materials Research Society, W4.1.1-W4.1.6.
Sergi, M. et al., "Proteins, recognition networks and developing interfaces for macromolecular biosensing," J. Mol. Recog., 2004, 17, 198-208.
Radosavljevic, M. et al., "Nonvolatile Molecular Memory Elements Based on Ambipolar Nanotube Field Effect Transistors," Nano Lett., 2002, 2(7), 761-764.
Pengfei Qi et al., "Toward Large Arrays of Multiplex Functionalized Carbon Nanotube sensors for Highly Sensitive and Selective Molecular Detection," Nano Lett., 2003, 3, 347-351.
Patel, D.J. et al., "Structure, recognition and adaptive binding in RNA aptamer complexes," J. Mol. Biol., 1997, 272, 645-664.
Parrinello, M. et al., "Polymorphic transitions in single crystals: a new molecular dynamics method," J. Appl. Phys., 1981, 52, 7182-7190.
Novak, J.P. et al., "Nerve agent detection using networks of single-walled carbon nanotubes," Appl. Phys. Lett., 2003, 83, 4026-4028.
Nakao, H. et al., "Transfer-Printing of Highly Aligned DNA Nanowires," J. Am. Chem. Soc., 2003, 125(24), 7162-7163.
Martel, R. et al., "Single- and Multi-wall carbon nanotube field-effect transistors," Applied Physics Letters, Oct. 26, 1998, 73(17), 2447-2449.
Kong, J. et al., "Nanotube Molecular Wires as Chemical Sensors," Science, 2000, 287, 622-625.
Keren, K. et al., "DNA-Templated Carbon Nanotube Field-Effect Transistor", Science, 2003, vol. 302, pp. 1380-1382.
Hahm, J.I. et al., "Direct Ultrasensitive Electrical Detection of DNA and DNA Sequence Variations Using Nanowire Nanosensors," 2004, 4, 51-54.
Gouma, P. et al., "Novel Materials and Applications of Electronic Noses and Tongues," MRS Bulletin, Oct. 2004, 697-702.
Gelperin, A. et al., "Report No. FED003A03GELPE to U.S. Army Research Office", Jun. 8, 2010, pp. 1-7.
Gelperin et al., "Nanotube-based sensor arrays for clinical breath analysis", J. Breath Res., Sep. 8, 2008, vol. 2, 037015, pp. 1-6.
Gao, H. et al., "Stimulation of DNA-Nanotube Interactions," Annu. Rev. Mater. Res., 2004, 34, 123-150.
Freitag, M. et al., "Role of Single Defects in Electronic Transport through Carbon Nanotube Field-Effect Transistors," Phys. Rev. Lett., 2002, 89(21), 216801.
D'Amico, A. and Di Natale, C., "Electronic Nose Applications," Nose Summer School, Lloret de Mar, Oct. 2-6, 2000, University of Roma Tor Vergata.
Chopra, S. et al., "Selective gas detection using a carbon nanotube sensor", Appl. Phys. Lett., 2003, vol. 83, No. 11, p. 2280.
Chen, R.J. et al., "Noncovalent functionalization of carbon nanotubes for highly specific electronic biosensors," Proc. Natl. Acad. Sci. USA, 2003, 100, 4984-4989.
Chen, R.J. et al., "An Investigation of the Mechanisms of Electronic Sensing of Protein Adsorption on Carbon Nanotube Devices," J. Am. Chem. Soc., 2004, 126, 1563-1568.
Breaker, R.R., "Natural and engineered nucleic acids as tools to explore biology," Nature, 2004, 432, 838-845.
Bradley, K. et al., "Short-channel effects in contact-passivated nanotube chemical sensors," Appl. Phys. Lett., 2003, 3821-3823.
Bradley, K. et al., "Charge Transfer from Ammonia Physisorbed on Nanotubes," Phys. Rev. Lett., Nov. 2003, 91(21), 218301-1 to 218301-4.
Berendsen, H.J. et al., "Molecular dynamics with coupling to an external bath," J. Chem. Phys., 1984, 81, 3684-3690.
Barone, P.W. et al., "Near-infrared optical sensors based on single-walled carbon nanotubes," Nat. Mater., 2005, 4, 86-92.
Agarwal et al., Immobilization of Histidine-Tagged Proteins on Nickel by Electrochemical Dip Pen Nanolithography, Dec. 20, 2002, J. Am. Chem. Soc. 125:7408-7412 (Year: 2002).

* cited by examiner

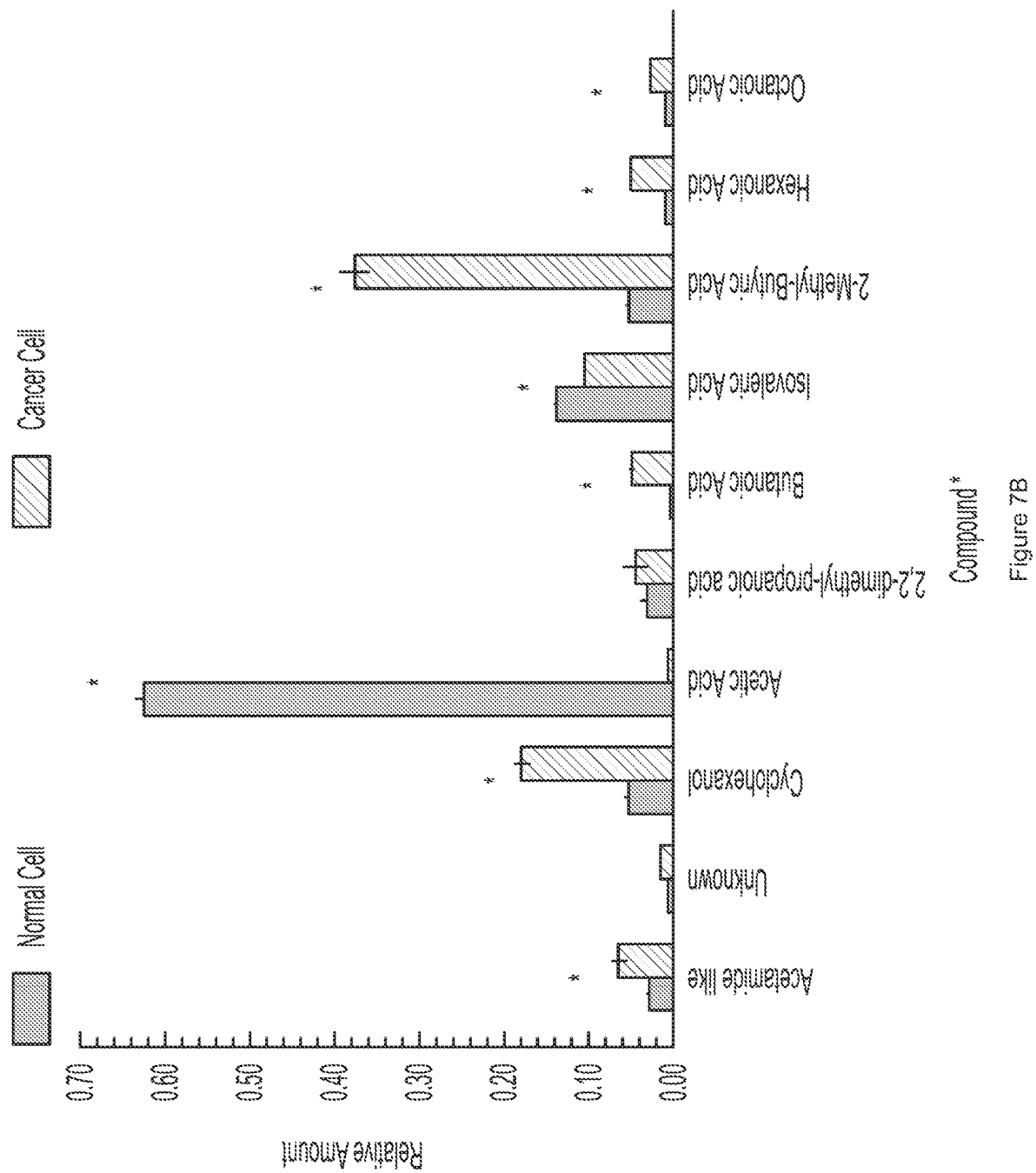

| Surface functional groups | | Protein functional groups | Product | |
|---|---|---|---|---|
| NHS ester [----] | ![NHS ester structure] | H$_2$NR | ![amide product] | amide |
| aldehyde [----] | ![aldehyde structure] | H$_2$NR | ![imine product] | imine |
| isothiocyanate [-] | —N=C=S | H$_2$NR | ![thiourea product] | thiourea |
| epoxide [--,--,--] | ![epoxide structure] | H$_2$NR | ![aminoalcohol product] | aminoalcohol |
| amine [--,--,[-]] | —NH$_2$ | HO(O)CCH$_2$R | ![amide product] | amide |

Figure 15

VOLATILE ORGANIC COMPOUND-BASED DIAGNOSTIC SYSTEMS AND METHODS

CROSS-REFERENCE TO RELATED APPLICATIONS

This application is the National Stage Application of International Patent. Application No. PCT/US2015/048343, filed Sep. 3, 2015, which claims the benefit of and priority to U.S. Patent Application No. 62/046,466, "volatile Organic Compound-Based Diagnostic Systems and Methods" (filed Sep. 5, 2014), the entirety of which application is incorporated by reference herein for any and all purposes.

SEQUENCE LISTING

The instant application contains a Sequence Listing which has been submitted electronically in ASCII format and is hereby incorporated by reference in its entirety. Said ASCII copy, created on Jun. 25, 2018, is named 103241_006185_14-7186_SL.txt and is 1,582 bytes in size.

TECHNICAL FIELD

The present disclosure relates to the field of detection of volatile compounds related to biomolecules and disease states and to the field of solid-state detector devices.

BACKGROUND

Cancer is a well-known, lethal disease, and ovarian cancer is the most lethal of the gynecological cancers and the fourth leading cause of cancer death in women. When diagnosed early, ovarian cancer has a favorable cure rate; however, more than 80% of patients are diagnosed at a late stage when even aggressive treatment is unable to effect a cure. Any advance that can lead to more accurate detection of ovarian cancer in its early stages would have a great impact on overall survival.

Despite extensive investigation, however, there is at present no sufficiently accurate screening test for early detection of cancer, particularly in patients of average risk. Accordingly, there is a need in the art for methods of screening samples for cancer (ovarian cancer in particular) and other disease states.

SUMMARY

In meeting the disclosed challenges, in one aspect the present disclosure provides detection devices, the devices comprising a semiconductor and a detection moiety in electronic communication with one another, the detection moiety being configured to detect one or more volatile organic compounds present in a biological sample; and a sensor chamber, the device being configured such that the detection moiety is capable of fluid communication with the interior of the sensor chamber.

In another aspect, the present disclosure provides methods, comprising: exposing a device (e.g., according to the present disclosure) to an atmosphere above a biological sample from a patient, the atmosphere comprising one or more volatile organic compounds of the sample; and detecting a signal, a change in signal, or both related to exposing the device to the atmosphere.

The present disclosure also provides methods, comprising: exposing a device (e.g., according to the present disclosure) to an atmosphere above a biological sample from a patient, the atmosphere comprising one or more volatile organic compounds of the sample; and detecting a signal, a change in signal, or both related to exposing the device to the atmosphere.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIGS. 7A and 7B. VOCs in the headspace above cell culture supernatants collected from normal ovarian epithelial cells or OVCAR3 cells. FIG. 7A shows most abundant compounds; FIG. 7B shows compounds at lower concentrations; * =p≤0.001.

FIG. 14A provides a schematic of interdigitated electrodes for FET with channel width 10 µm and a channel length of 1 mm. FIG. 14B provides an Atomic Force Microscope image of the channel region of a CNT FET. A sparse network of CNTs bridges the gap between the electrodes. FIG. 14C provides a photograph of a FET sensor array consisting of 100 ssDNA CNT FET devices. The interdigitated channel regions are on the left side of the chip, while contact pads extend to the left. Ten sets of 10 devices each are spatially separated for independent functionalization with a specific DNA oligomer.

FIG. 15 presents exemplary linkage chemistries that may be used to link a detection moiety to a substrate.

DETAILED DESCRIPTION OF ILLUSTRATIVE EMBODIMENTS

The present invention can be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, can also be provided in combination in a single embodiment. Conversely, various features of the invention that are, for brevity, described in the context of a single embodiment, can also be provided separately or in any subcombination. Further, reference to values stated in ranges include each and every value within that range. Any documents cited herein are incorporated herein by reference in their entireties for any and all purposes. It should also be understood that a reference to a particular testing condition (e.g., testing on ovarian cancer) is illustrative only and does not limit the disclosed technology to that particular condition.

Ovarian cancer is the most lethal of the gynecological cancers and the fourth leading cause of cancer death in women. When diagnosed early, ovarian cancer has a favorable cure rate; however, more than 80% of patients are diagnosed at a late stage, when even aggressive treatment is unable to effect a cure. Any advance that can lead to more accurate detection of ovarian cancer in its early stages can have a great impact on overall survival. But despite extensive investigation, there is no sufficiently accurate screening test for early detection of ovarian cancer in women of average risk. Studies suggesting that early diagnosis is possible using serum proteinaceous biomarkers appear to be controversial and disputed.

Figure 16:
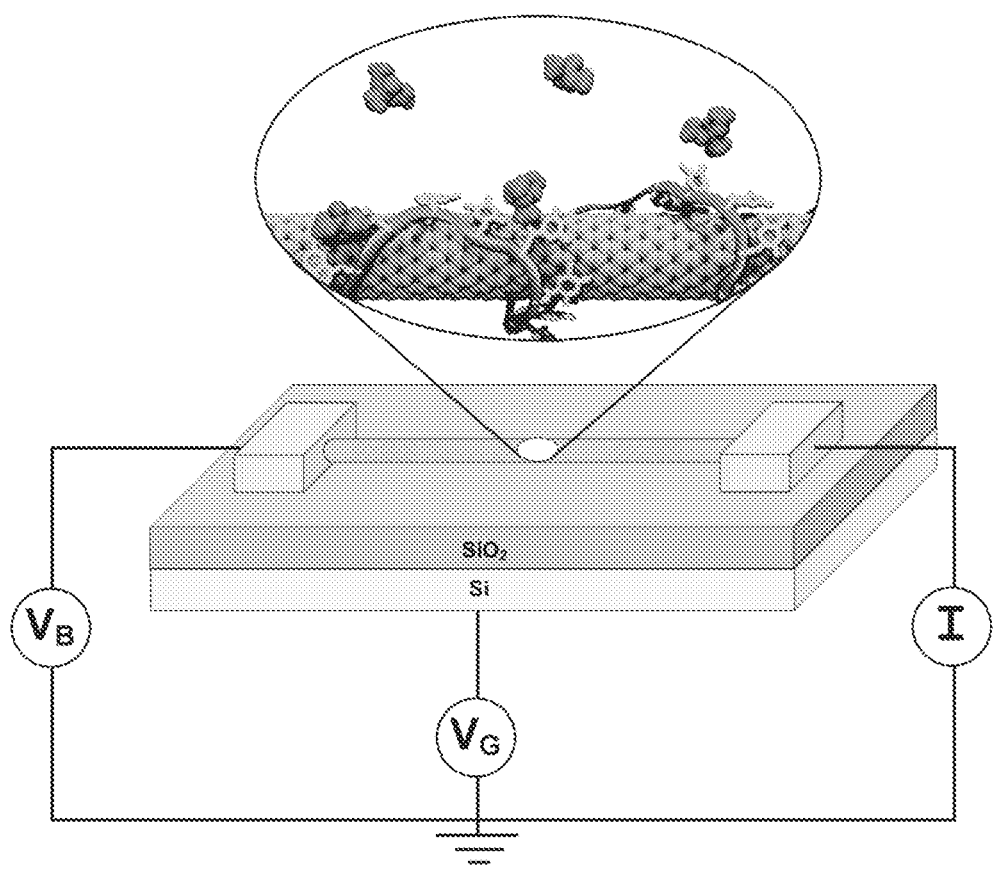
FIG. 16 presents an exemplary embodiment in which a single nanotube connects two electrodes; as shown, a detector moiety (e.g., a polynucleotide) is in electronic communication with the nanotube.

In one embodiment, the present disclosure provides detection devices. The devices may include a semiconductor material (e.g., doped silicon, nanotubes—including carbon nanotubes, graphene, and the like) and a detection moiety in electronic communication with one another. One such embodiment is shown in FIG. 16. As shown in that figure, a device is constructed with two electrodes (not labeled) atop a SiO2 substrate (which in turn is atop a Si substrate). A carbon nanotube (magnified) is present between the two electrodes, and a detector moiety (e.g., a polynucleotide) is in electronic communication with the nanotube. Molecules of interest interact (e.g., bind) with the detector moiety, and changes in signal related to those interactions are then collected and further analyzed. As shown in the figure, voltage and current sources are in electronic communication with the device.

The detection moiety may be configured (or chosen, selected, or even modified) to detect one or more volatile organic compounds present in a biological sample. The devices may also include a sensor chamber (e.g., an enclosed vessel, such as a cup, tub, tube, beaker, cylinder, dish, bowl, or other such vessel). The device may be configured such that the detection moiety is capable of fluid communication with the interior of the sensor chamber. As one example, the detection moiety may be disposed in the sensor chamber. Alternatively, one or both of the moiety and chamber may be capable of motion relative to the other, e.g., such that the moiety may be insertable into the chamber, or even such that the chamber may be moveable so as to enclose the detection moiety.

In one embodiment, the chamber is sealed against the external environment in order to retain the VOCs. The detection moiety or moieties may be located in the headspace of the sensor chamber so as to place them into contact with the VOCs when the VOCs are present.

It should be understood that the present disclosure provides kits. The kits may include a device that comprises a detector moiety, a substrate (in electronic communication with the detector moiety). The device may include one or more connections in electronic communication with the substrate. The device may also include a chamber configured to contain a sample from which the detection moiety may detect VOCs. The chamber may even be a syringe or other similar chamber into which a user may introduce (e.g., via puncture, via pipetting, injecting, or by other methods) a sample. The kit may also include a heater configured to heat the sample within the chamber to encourage release of VOCs from the fluid sample; a kit may also include a plunger, membrane, or other part that a user may manipulate to change the pressure within the chamber. The kit may include a reader device (e.g., a display or even an LED or other indicator) that provides information regarding one or more signals from the detection moiety, e.g., a signal that relates to the presence or absence of a VOC to which the detection moiety is sensitive. The kit may also include a power source used to provide power to the device. In this manner, the present disclosure provides kits that may be used as an on-site detection system for one or more VOCs that are suggestive of a condition. The kit may include instructions and other documentation so as to enable use by a variety of personnel.

A variety of materials are considered suitable semiconductors. The semiconductor may include, e.g., graphene, a carbon nanotube (i.e., one or more carbon nanotubes), $MoS_2$, silicon, zinc oxide, $WS_2$, silicon, germanium, gallium arsenide, indium phosphide, gallium nitride, or any combination thereof. Graphene is considered an especially suitable semiconductor, as are carbon nanotubes.

The semiconductor may be tubular, planar, curved, plate-shaped, or of virtually any other configuration, e.g. a ribbon, a strip, a ring, a loop, a C-shape, a T-shape, an L-shape, a U-shape, or other configuration. The semiconductor may be in electronic communication with a conductor, e.g., a wire, lead, pin, or other conductor (e.g., a metal). Nanotubes and nanowires are considered especially suitable.

A semiconductor substrate may have a cross-sectional dimension (e.g., width, length height, diameter, thickness, radius, and the like) in the range of from 0.5 nm to 10 cm, from 1 nm to 5 cm, from 10 nm to 1 cm, from 100 nm to 1 mm, or even from 50 nm to 0.5 mm. A semiconductor substrate may be individually addressable. In some embodiments, a device may include one, two, three, or more substrates in electronic communication with one another.

Devices according to the present disclosure may include one or more valves configured to modulate fluid communication between the detection moiety and the interior of the sensor chamber. The valve may be manually actuated or actuated in an automatic fashion, e.g., by a computer controlled configured to open (or close) the valve in response to a particular signal or control. Such a signal may be related to a level of an analyte, the passage of time, the position of a component, an amount of material, or some combination thereof.

A device may include a sample chamber. The sample chamber may be capable of fluidic communication with the interior of the sensor chamber. For example, a biological sample may be placed in the sample chamber, and that sample chamber may in turn be in fluid communication with the sensor chamber. It should be understood that in some embodiments, the sensor chamber is configured to contain a biological sample. In some embodiments, the detection moiety may be capable of fluid communication with a headspace of the sensor chamber. As described elsewhere herein, the detection moiety may be disposed within the sensor chamber. A chamber may be plastic, metal, flexible, rigid, or any combination thereof. The chamber may be removeable or separable from the device. The chamber may include one or more inlet ports or other entry points at which a sample may be introduced. A detector may also be inserted into the chamber by way of an inlet or other entry port. The present disclosure should be understood as including kits, which kits may include a chamber, a detection moiety, and a semiconductor. A user may assemble together one or more of these components.

Figure 17:
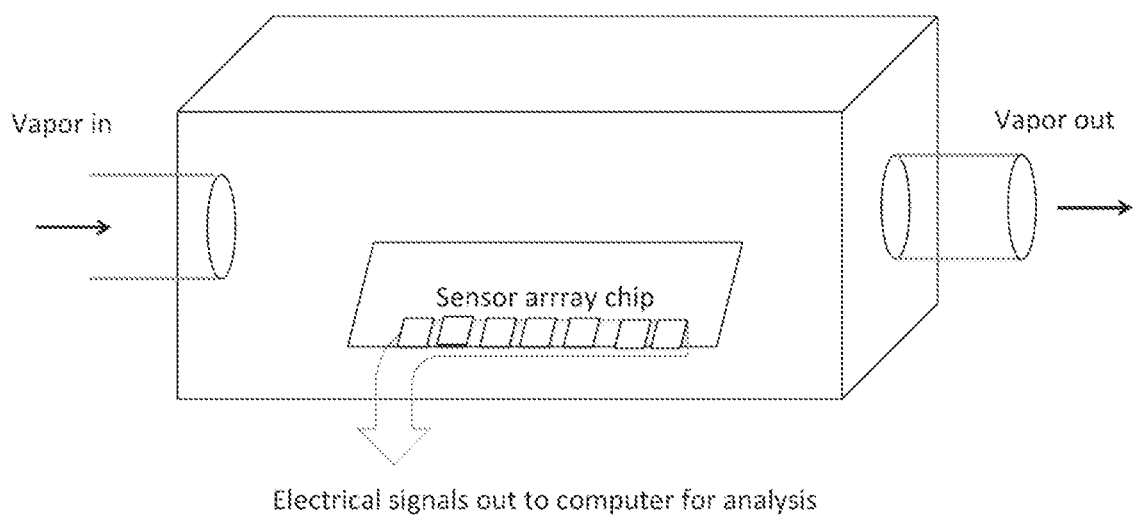
FIG. 17 presents an exemplary embodiment of an array of sensors according to the present disclosure placed in a chamber where a vapor sample is flowed across the array and signals from the array are communicated to a computer or other device for further analysis.

An exemplary device is shown in FIG. 17. As shown in that figure, a sensor array chip may be disposed within a chamber. A sample is introduced to the chamber via the inlet ("Vapor in") and then contacts the sensor or sensors on the chip. The sample interacts with the various components of the sample which in turn generates one or more signals that are then communicated to a computer or other device for further analysis. The chamber may include an outlet ("Vapor out") to allow the sample to exit. It should be understood that a sample may be liquid and then be vaporized (or partially vaporized) in the chamber so as to release VOCs from the sample. The detector may be in the headspace of the chamber so as to allow the detector to contact VOCs without also contacting a liquid sample.

A device may include two or more detector moieties that differ from one another in structure. A detection moiety may include a polynucleotide, a polypeptide, a nucleic acid-polypeptide complex, a carbohydrate, an aptamer, a ribozyme, and any and all homologs, analogs, conjugates, or derivatives thereof, as well as mixtures thereof, or any combination thereof. A detection moiety may be a protein, e.g., an olfactory receptor protein or a water soluble variant of an olfactory receptor protein. Olfactory proteins and their variants are considered especially suitable detection moieties.

A detection moiety may be a polyonucleotide, as described. A polynucleotide may be one or more of, for example, 5' GAG TCT GTG GAG GAG GTA GTC 3' (SEQ ID NO: 1), 5' CTT CTG TCT TGA TGT TTG TCA AAC 3' (SEQ ID NO: 2), 5' CCC GTT GGT ATG GGA GTT GAG TGC 3' (SEQ ID NO: 3), 5' GTA CGG ACT GTG AAT GCG CGT TAG 3' (SEQ ID NO: 4), or any combination thereof. A polynucleotide may be randomly selected or generated, but may also be preselected. A polynucleotide may include 2, 5, 10, 20, 50, 100, 150, 200, or even 1000 bases, as well as all intermediate values. Likewise, a polypeptide may include, e.g., from 2 to 50 amino acids. It should be understood as explained below that proteins and polypeptides are both suitable detector moieties.

A detection moiety may also be a polypeptide, such as a protein or other such structure. A detection moiety may be a monomer or polymer; copolymers (including block copolymers, graft copolymers, and the like) are considered suitable. Receptors and ligands are also considered suitable detector moieties. Detector moieties that exist in connection with olfactory systems (e.g., olfactory proteins from mammals) are considered especially suitable.

Detection moieties may be configured to detect one or more pre-selected volatile organic compounds. Exemplary such compounds may include dimethylsulfone, 3,4-dimethyl benzaldehyde, an alkyl substituted pyridine, cyclohexanone, 2-pentylfuran, caprolactam, or any combination thereof. VOCs that show differences between patient groups and controls (e.g., 2-methylpyridine) are considered particularly suitable.

The disclosed devices may include a monitor, which may be in electronic communication with the detector moiety. The monitor may be configured to detect a signal, a change in signal, or both related to an interaction between the detection moiety and a volatile organic compound of a biological sample. Suitable such signals may include a current, voltage, a current-gate voltage, resistance, or any changes or combination thereof.

Optical or visual signals may also be monitored. Such signals include intensity, wavelength, and the like; as one example, a user might illuminate a detection moiety with a laser or other beam so as to detect optical signal changes related to an interaction between the detection moiety and a VOC. Changes in signals may include a change in current, a change in voltage, a change in resistance, a change in current-gate voltage characteristic, a change in intensity, a change in wavelength, or any combination thereof.

A detection moiety may be covalently bound to the semiconductor, e.g., by using an amide, thiol, peptide, histidine tag linkage, or, e.g., a linkage between nickel-nitriloacetic acid group and a histidine residue. Linkages that include a chitin binding protein, a maltose binding protein, glutathione-S-transferase, an epitope tage, or any combination thereof are also suitable, as are cysteine-graphene linkages, amide bonds (e.g., between a protein and graphene), an imine bond (e.g., between a protein and graphene), a thiourea bond (e.g., between a protein and graphene), an aminoalcohol bond (e.g., between a protein and graphene), and the like.

In some embodiments, a protein may be bound to graphene by a peptide sequence. In one embodiment, a protein may be attached to graphene by adding a specific peptide sequence, such as one that is identified using a phase display peptide library. Graphene may itself be modified to comprise a moiety to facilitate attachment. Such moieties include sugars, antibodies, a chitin binding protein, a maltose binding protein, glutathione-S-transferase (GST), an epitope tag, and the like. Suitable epitope tags include a V5-tag, a c-myc-tag, a HA-tag, or any combination thereof. Proteins used in the disclosed devices may include a reactive amino acid, which includes photoreactive amino acids.

The graphene of the disclosed devices may include a diimide-activated amidation between the graphene and biomolecules. The devices may also include a cysteine-graphene linkage between the graphene and biomolecules. Such a linkage may be effected by treatment with diazonium, EDC NHS, PDEA aka 2-(2-pyrdinyldithio) ethaneamine, with a thiol-bearing region of the protein.

A variety of linkages may be used to connect a biomolecule to graphene, including an amide bond between the biomolecules and graphene, an imine bond between the biomolecule and graphene, a thiourea bond between the biomolecule and graphene, an aminoalcohol bond between the biomolecule and graphene.

Ionic bonds may be used as well. A detection moiety may be bound to the semiconductor by pi-pi orbital interaction, by hydrogen bonding, by coordination bonds, or by other bonds known to those in the art. Still more exemplary linkages are shown in non-limiting FIG. 15.

In some embodiments, the device may be configured to encourage release of one or more VOCs from a sample. A device may include a heater configured to encourage release of one or more volatile organic compounds present in the biological sample. A device may also include a source of reduced pressure configured to encourage release of one or more volatile organic compounds present in the biological sample. Such a source may be a vacuum device (including automated vacuum devices as well as a plunger, membrane, or other part that a user can move), and the pressure may be 99%, 90%, 50%, 10%, 5%, 1%, or even 0.5% of atmospheric pressure. The pressure, heat, or addition of material (e.g., salt, as described elsewhere herein) may be modulated singly or together so as to effect release of one or more VOCs from the biological sample. The source of reduced pressure is suitably configured to reduce the pressure exerted on the biological sample such that VOCs are released (or to speed VOC release) from the sample. Likewise, the heater is suitably configured to increase the temperature of the sample (or nearby to the sample) such that VOCs are released (or to speed VOC release) from the sample.

A device may also include a volatile organic compound from a biological sample in interaction with the detection moiety. The interaction may be a chemical bond (e.g., covalent, ionic, hydrogen bonding, coordination) or some electronic interaction. As described elsewhere herein, such an interaction suitably gives rise to a change in signal (e.g., current) related to the interaction between the VOC and the detection moiety.

It should be understood that the present devices may be configured to assess the presence of one, two, three, or more VOCs. A device may also include an array of semiconductors and detection moieties such that the device is configured to assess the presence (or absence) of multiple VOCs. The devices may also be configured to assess the presence (or absence) of one, two, or multiple disease states. As one example, a device might include a first set of detector moieties that are configured to detect the presences of VOC1, VOC2, and VOC3, which three VOCs are characteristic markers for ovarian cancer. The device may include a second set of detector moieties that are configured to detect the presences of VOC4, VOC5, and VOC6, which VOCs are characteristic markers for lung cancer. The device may then be used to assess the status of a biological sample for ovarian and another cancer, e.g., breast cancer. It should be understood that the present disclosure is not limited to ovarian cancer, as the technology may be applied to other cancers, e.g., lung cancer, gynecologic carcinomas, and the like.

The present disclosure also provides methods. The methods may include exposing a device according to the present disclosure to an atmosphere above a biological sample from a patient, the atmosphere comprising one or more volatile organic compounds of the sample; and detecting a signal, a change in signal, or both related to exposing the device to the atmosphere.

The methods may further include adding a material to the biological sample that encourages one or more volatile organic compounds from the sample into the atmosphere, heating the biological sample, applying a reduced pressure to the biological sample, or any combination thereof. The material may be a salt, e.g., NaCl, KCl, CaCl, or other salt. The methods may also include heating the sample to as to encourage release of VOCs from the sample. The heating may be performed to raise the sample temperature by 1 deg. C., 5 deg. C., 10 deg. C., 20 deg. C., 50 deg. C., 75 deg. C., or more. A sample may be brought to boil in some embodiments.

As described elsewhere herein, suitable signals may include a current, voltage, resistance, current-gate voltage characteristic or any combination thereof. The change in signal may include a change in current, a change in voltage, a change in resistance, or any combination thereof. As described in the non-limiting examples presented herein, changes in current are considered particularly suitable.

The methods may further include correlating the signal, the change in signal, or both, to a disease state of the patient. For example, a change in a current signal may correlate to the presence of a cancer-marking VOC in the atmosphere to which a device has been contacted.

A disease state may be cancer, a gastrointestinal disorder, an infection, or other disease. Cancer disease states include all forms of cancer, e.g., ovarian cancer, breast cancer, lung cancer, prostate cancer, or any combination thereof.

Correlating may include, e.g., comparing the signal, change in signal, or both to a signal, a change in signal, or both to a standard. A standard may be a well patient, a disease state patient, or other comparator. The correlation may include differences in signal, differences in rate of change of signal, absolute rates of change of signal, integration (area-under-curve) of signal vs. time, and the like.

The methods may include clearing the device so as to return the device to a baseline. The clearing may be performed so as to return the device to a "clean" state from which the device may be reused. Clearing may include applying a carrier fluid, e.g., ambient or breathing air, nitrogen, or argon, purified air, or some combination thereof. Clearing may also include applying a fluid (e.g., water, an electrolyte, a solvent, and the like) that releases VOCs from the detection moieties so that the detection moieties may be used in a later analysis. A system may include a routine that zeros the signal of a 'clear' detection moiety so that each analysis begins with a 'zero' baseline signal.

A variety of biological samples (including bodily fluids) may be used. For example, whole blood, serum, plasma, saliva, vaginal secretions, urine, mucus, phlegm, semen, cell culture media, cell culture supernatant, or any combination thereof. Serum is considered particularly suitable, but is not the exclusive biological sample suitable for the disclosed technology.

Additionally provided are methods, the methods including effecting release of one or more volatile organic compounds from a biological sample into an atmosphere; contacting the atmosphere and a detection moiety in electronic communication with a semiconductor; and detecting a signal related to the contacting, detecting a change in signal related to the contacting, or both.

Suitable detection moieties and semiconductors are described elsewhere herein. Detecting a signal, a change in signal, or both, may be related to exposing the device to the atmosphere. The effecting may include heating, reducing pressure, adding an agent that encourages one or more volatile organic compounds from the sample into the atmosphere, or any combination thereof. As described elsewhere herein, the signal, the change in signal, or both, may be related to interaction between a volatile organic compound and the detection moiety.

The methods may further include comparing the signal related to the contacting, the change in signal related to the contacting, or both, to a standard. The methods may also include correlating the signal, the change in signal, or both, to a disease state, e.g., cancer or other disease state.

Some exemplary analyses are provided of the VOC signature of ovarian cancer based on serum samples collected from ovarian cancer patients, patients with benign ovarian tumors, and age-matched, healthy controls. Measurements of pooled serum samples from these three populations show that their respective odor profiles can be differentiated using DNA-decorated carbon nanotube vapor sensors (DNA-NT). This finding was confirmed by experiments based on the analytical technique solid-phase microextraction gas chromatography/mass spectrometry (SPME-GC/MS) and trained detection dogs, both of which showed discernable differences among samples derived from the three patient pools.

Cells release odorants that possess finite vapor pressures at body and/or ambient temperatures. These VOCs can be found emanating from all body fluids. As cells turn malignant, analysis of these odorants provides insight into cancer diagnosis. Thus, one may screen for ovarian cancer (or other conditions) through analysis of VOCs with advanced nanosensors such as DNA-NT.

Figure 1:
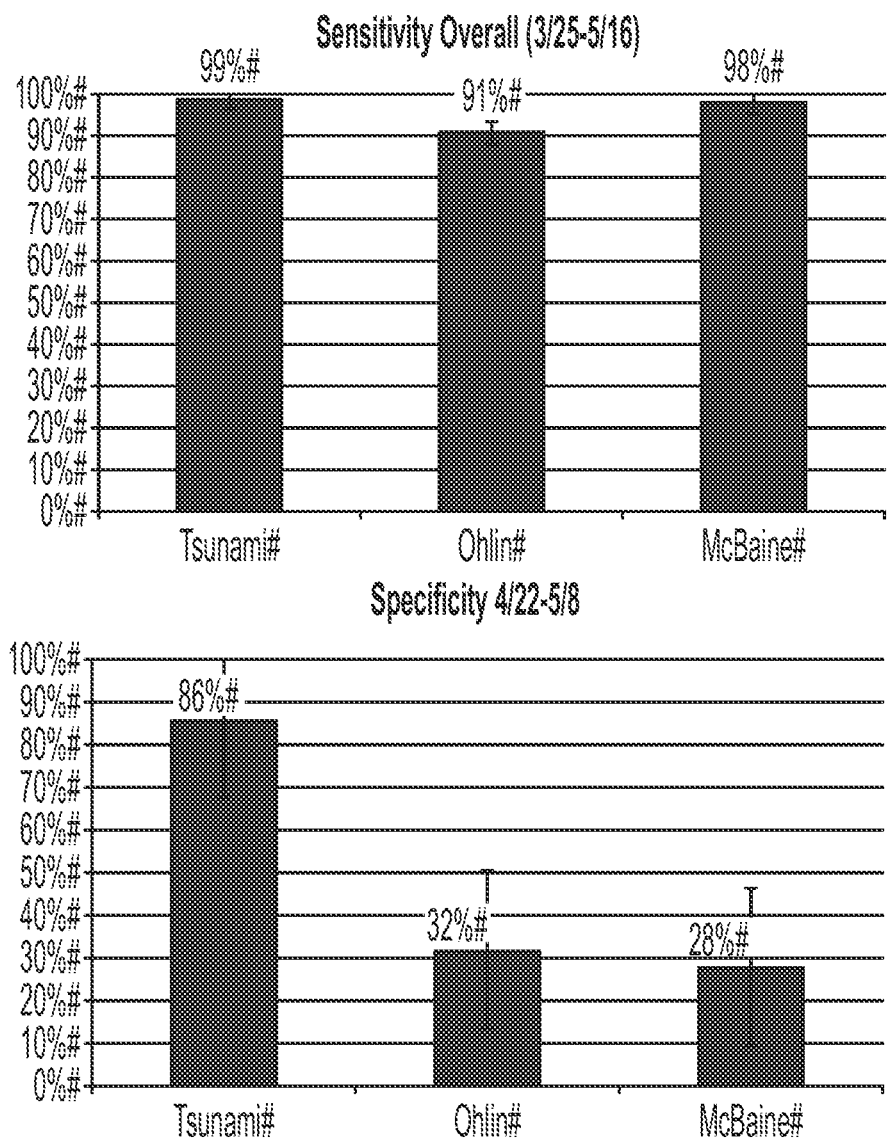
FIG. 1. Results of working dog training for ovarian cancer detection; testing against pooled plasma samples. The sensitivity is very high for all three dogs used.

Specific to ovarian cancer, dogs were trained to distinguish ovarian cancer tissues of various stages and grades from normal ovarian tissue and other gynecological malignancies with sensitivity and specificity over 95%; when trained on tissue, dogs were able to detect the VOC disturbances in peripheral blood samples with the same accuracy. Results from a study (FIG. 1) are consistent with these earlier reports and indicate high sensitivity and selectivity for pooled samples of plasma from ovarian cancer patients over pooled samples from health controls (n=10 for each).

Figure 2A:
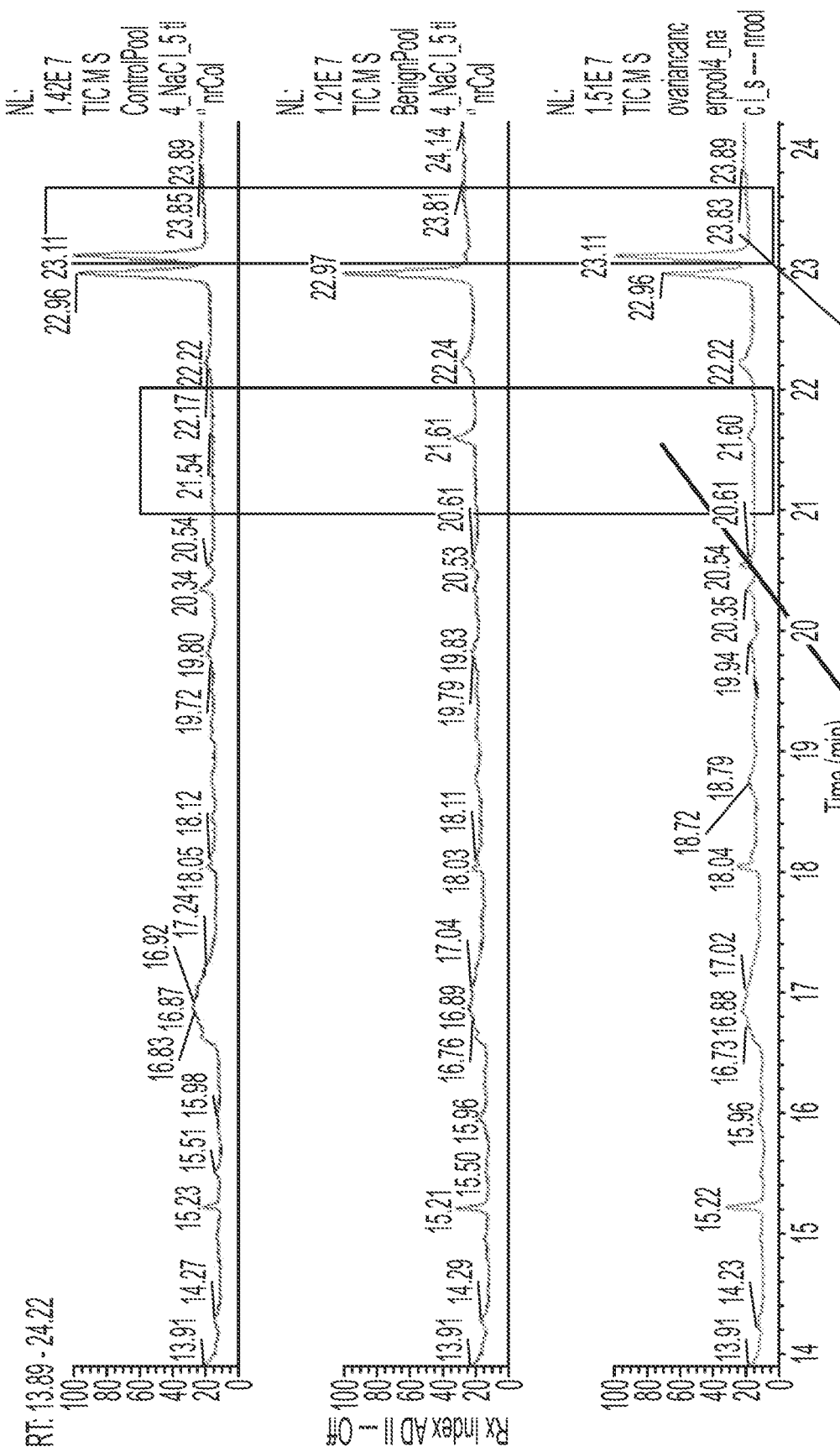
FIG. 2. The top three plots show differences in selected regions in the Total Ion Chromatographs obtained from analyses of SPME-collectedvolatile organic compounds (VOCs) from the three pools of samples (top: control; middle: benign growth; bottom: ovarian cancer). The bottom two plots show the mass spectrometry data for the two compounds that show the strongest differences. One is identified as dimethylsulfone and the second is a substituted benzaldehyde.
Figure 2B:
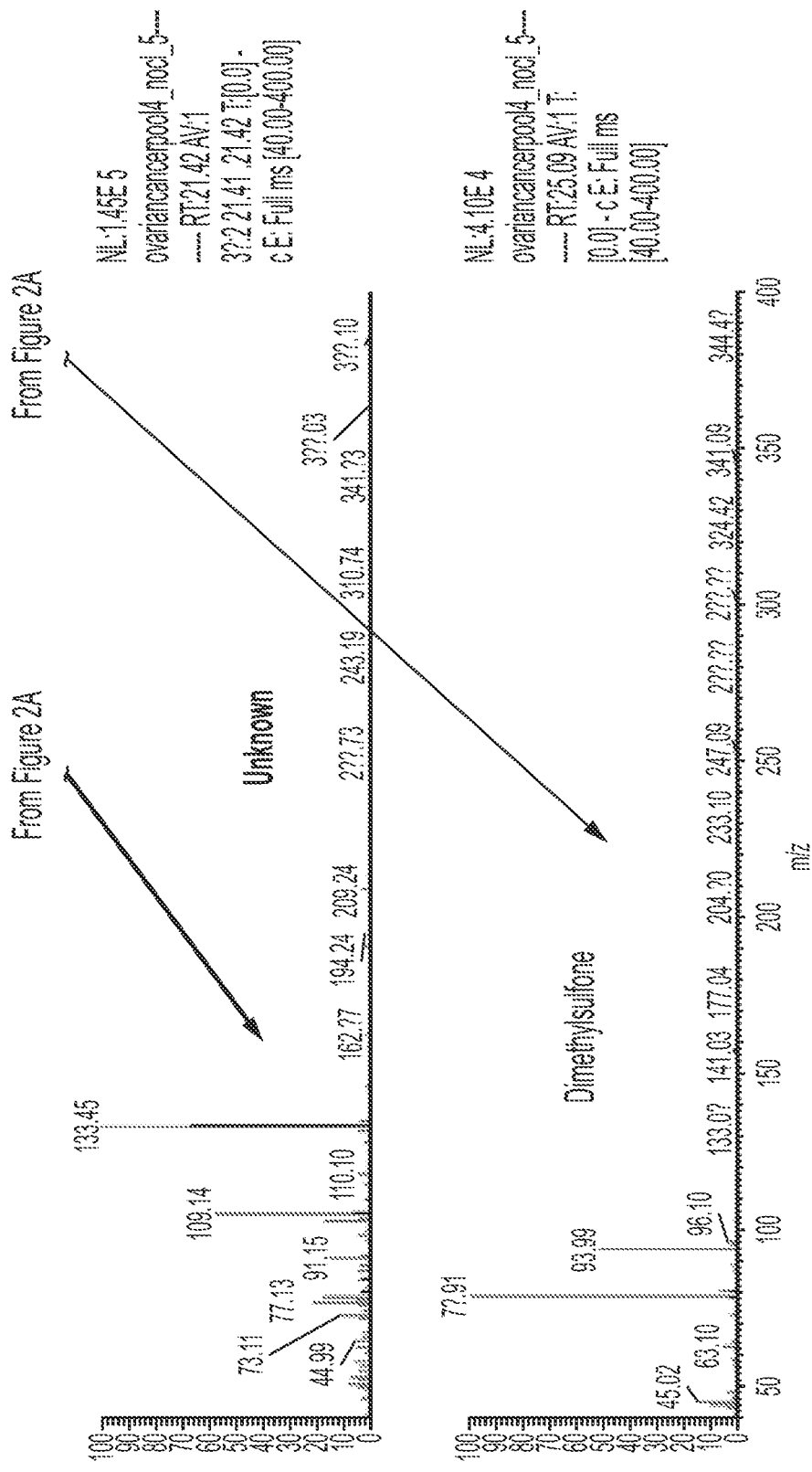

SPME-GC/MS is a sensitive method to collect, detect and identify the molecules in the VOC signature that distinguishes patients with ovarian cancer from controls. One may find differences in the VOC profiles for each category of pooled plasma samples from patients and controls (FIG. 2). Dimethylsulfone, a common metabolite of methionine, differed among groups with the largest amounts present in the cancer pool. Another observed difference related to an unknown compound at retention time ca. 21.60 minutes. The mass spectrum of this compound (FIG. 2) suggests—without being bound to any particular theory—that it is a substituted benzaldehyde. None is detected in controls.

Single-walled carbon nanotube field effect transistors (FETs) coated with single stranded DNA (DNA-NT) show a change in source-drain current upon exposure to VOCs and VOC mixtures. DNA-NT responses are controlled by the DNA base sequence. The sensor class is thus suited for an array with a number of sensors with uncorrelated odor responses, as required for an system with computational power approaching that of mammalian olfaction.

In one exemplary experiment, arrays of 56 devices each were fabricated in parallel on $Al_2O_3$ coated $Si/SiO_2$ wafers by first using photolithography/metallization to produce Cr/Au electrodes and then drop casting semiconducting-enriched (98%) nanotube solution (NanoIntegris Inc.) onto the chips. Washing, cleaning, and annealing steps were performed to remove surfactants and ensure electrical contact between the CNTs and gold electrodes. Finally, DNA functionalization was performed by pipetting a 100 μM DNA solution (Invitrogen Co.) onto the devices and allowing the DNA strands to diffuse to and bind onto the sidewalls of the CNTs. The DNA strands bind via the π-π stacking interaction between the DNA bases and the CNT surface; as described elsewhere herein, other electronic interactions are also suitable.

After 30 minutes, the DNA solution was blown off the chip with compressed nitrogen gas, removing unbound DNA, and the devices were ready to use. It should be understood that devices can be produced in various ways and still maintain the same basic characteristics. As but one example, carbon nanotubes could be grown by chemical vapor deposition or other methods, and DNA could be applied using any one of a number of spotting techniques.

Figure 3:
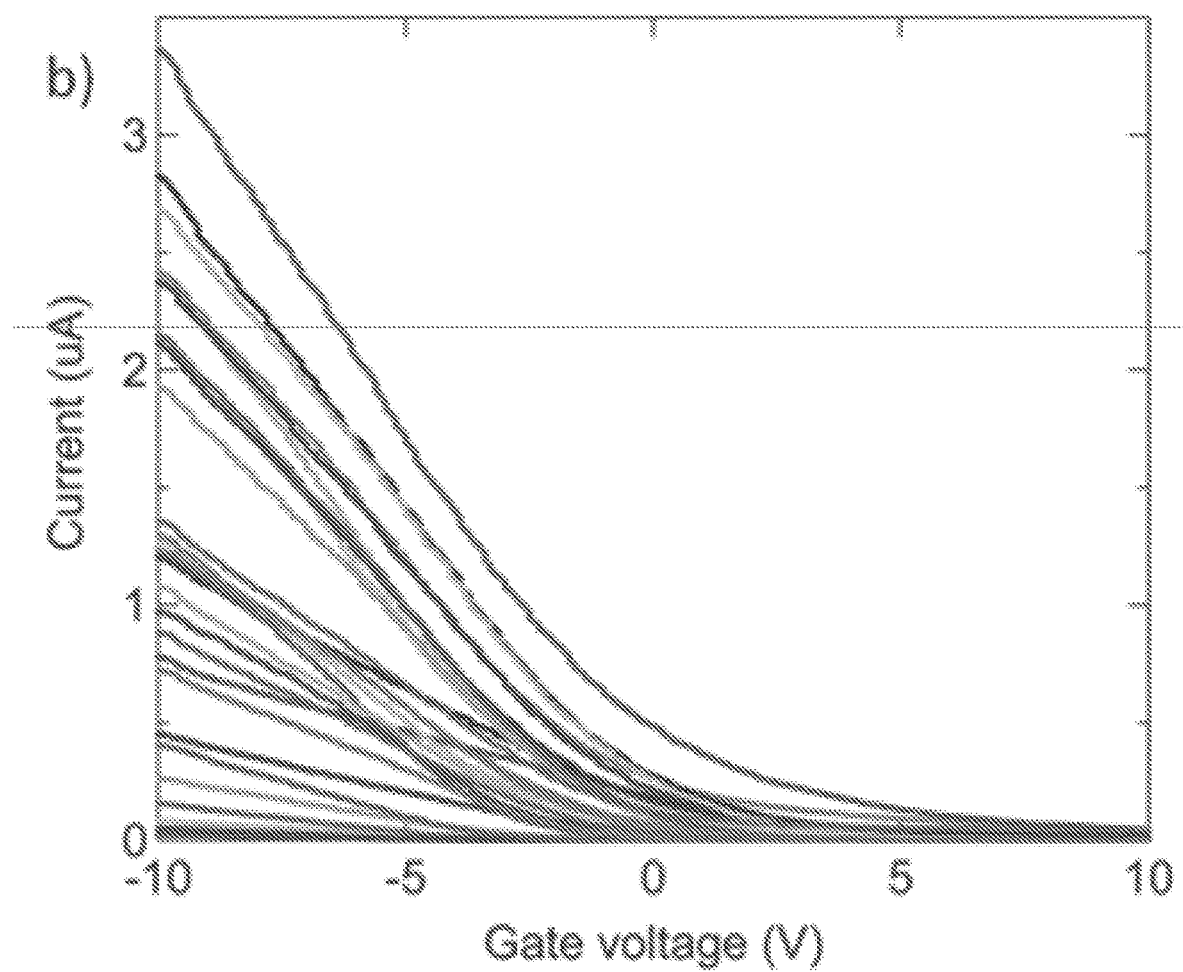
FIG. 3. Current vs. gate voltage for a typical array of 28 devices from one of the sensor arrays, measured with source-drain voltage of 100 mV.

Before the DNA functionalization and sensing experiment, the CNT devices were characterized electronically by conducting a three terminal current vs. gate voltage measurement using the global silicon back gate. As shown in FIG. 3, the devices showed reproducible p-type electronic behavior, with ~95% of the devices exhibiting on-off ratios exceeding 20 and a narrow range of turn-off voltages centered around zero volts.

To compare devices with different on-state currents, the sensor response is reported as the percentage change in the current $N/I_0$. The gate voltage was held fixed at −8 V for all vapor sensing measurements to maintain a high current level and transconductance, with the goal of maximizing the signal-to-noise ratio To increase the concentrations of VOCs in the headspace of the samples, 125 mg of NaCl was added to a 500 μL serum sample in a 25 mL two-neck round-bottom flask which makes the serum less hospitable for VOCs and drives them into the vapor phase. The sample was also heated to 45° C. and stirred vigorously with a miniature stir bar.

A mass flow controller (MFC) was connected to the inlet of the round-bottom and a check-valve was connected to the outlet, keeping the headspace isolated until any carrier gas was pulsed through. The closed headspace was left to accumulate volatiles for 30 minutes, after which nitrogen carrier gas was passed through the MFC, pushing a stream of VOCs from the serum sample out of the round-bottom towards the sensor chamber.

Experimental Procedure

Figure 4:
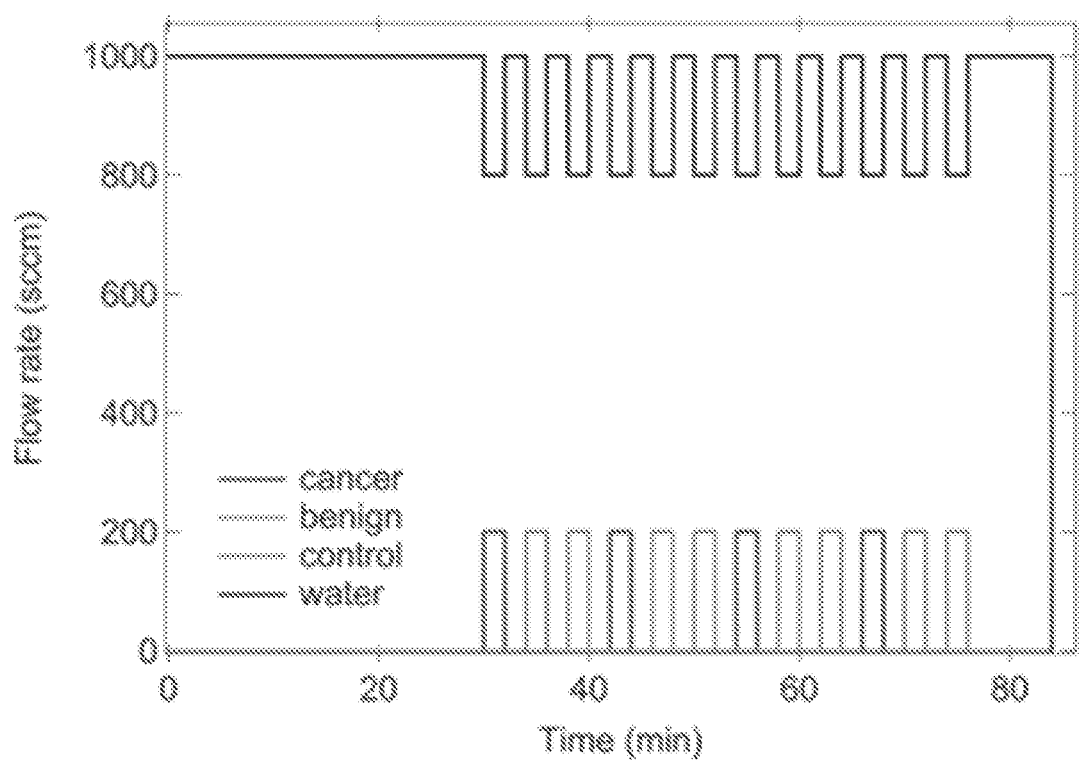
FIG. 4. The flow through each mass flow controller during the experiments. After a 30 minute settling period to build-up the headspace vapors, two minute pulses of vapor from the serum headspaces were alternated with two minute chamber flushes (cancer is bottom bars 1, 4, 7, 10; benign is bottom bars 2, 5, 8, 11; control is bottom bars 3, 6, 9, 12; and water is bars at top of figure).

An array of DNA-NT sensors was placed into a chamber of size 6 cm×2.5 cm×1 cm with electrical feedthroughs to allow the conduction of each sensor to be monitored. An inlet and outlet allowed the environment to be controlled. The 3 different pooled serum samples (cancer patients, patients with benign tumors, healthy controls) were tested in the same experimental run. The flow recipe used is shown in FIG. 4. For the first 30 minutes, water vapor from a bubbler was flown into the chamber. During this time, the headspace of each of the serum samples was closed off, and the salted serum samples were heated and stirred as described above, allowing the VOCs to build up in the headspace. After 30 minutes, headspace vapor from the first serum sample was pulsed into the sensor chamber for two minutes, followed by 2 min of flowing clean air carrier gas, which was determined to restore the sensor response to baseline. This cycle of 2 min of exposure to vapor and 2 min purging with clean air was repeated for the other two pooled plasma samples, and the full cycle of exposure to each of the plasma samples rate (200 sccm) and the relative humidity (100%) were constant through the entire experiment. While not necessary, one may keep the total flow rate and humidity constant to help ensure that all sensor signals were due to the presence of the volatiles from the serum and not a different environmental factor.

Vapor Sensing Results and Analysis

Figure 5:
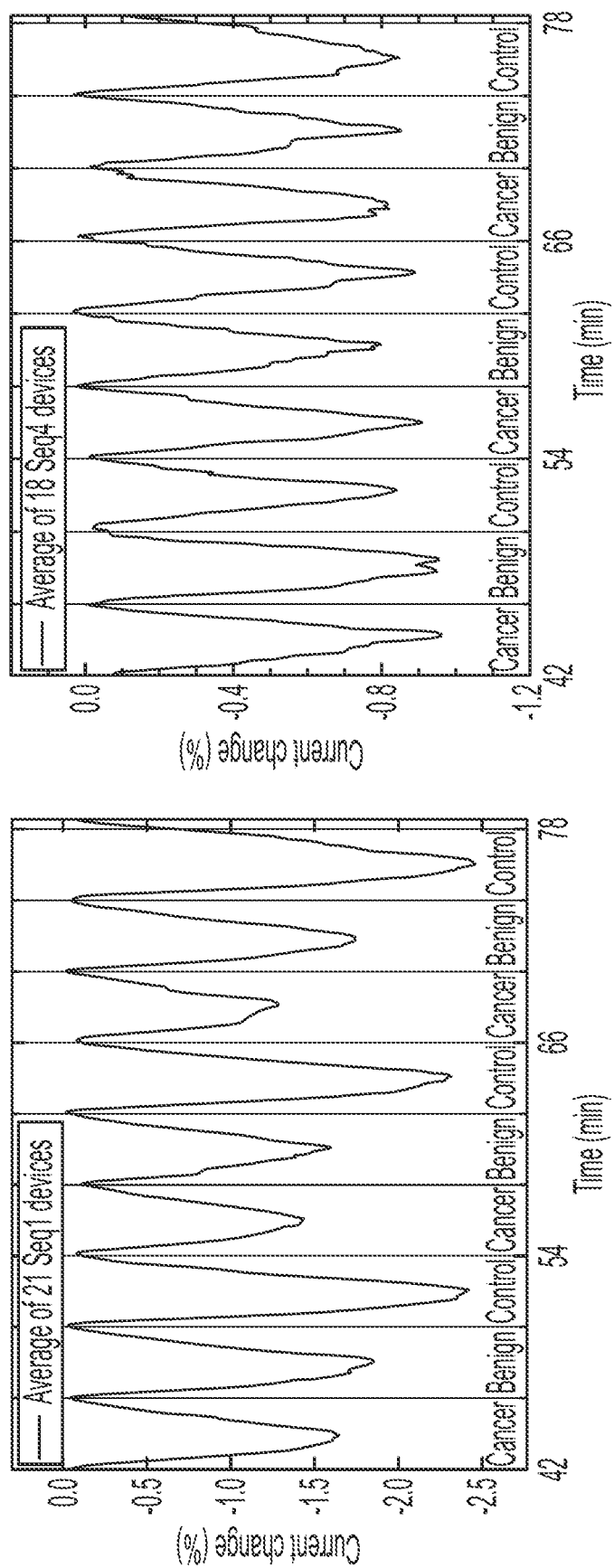
FIG. 5. Sensor responses for DNA-NT based on Seq1 (left) show a clear differentiation between the plasma samples ("Cancer", "Benign", and "Control"), while those based on Seq4 do not (right).

Data streams were collected from an array of 21 DNA/NT devices based on the same DNA sequence, and the measurements from the devices were averaged to enhance the signal-to-noise characteristics. DNA-NT based on DNA of different base sequences showed different behavior, as expected, as device responses are known to depend sensitively on the DNA base sequence. Responses of DNA-NT based on Seq1 showed strong differentiation between the three pooled plasma samples (FIG. 5, left panel). In contrast, DNA-NT based on Seq4 showed almost identical responses to the three samples tested.

Figure 6:
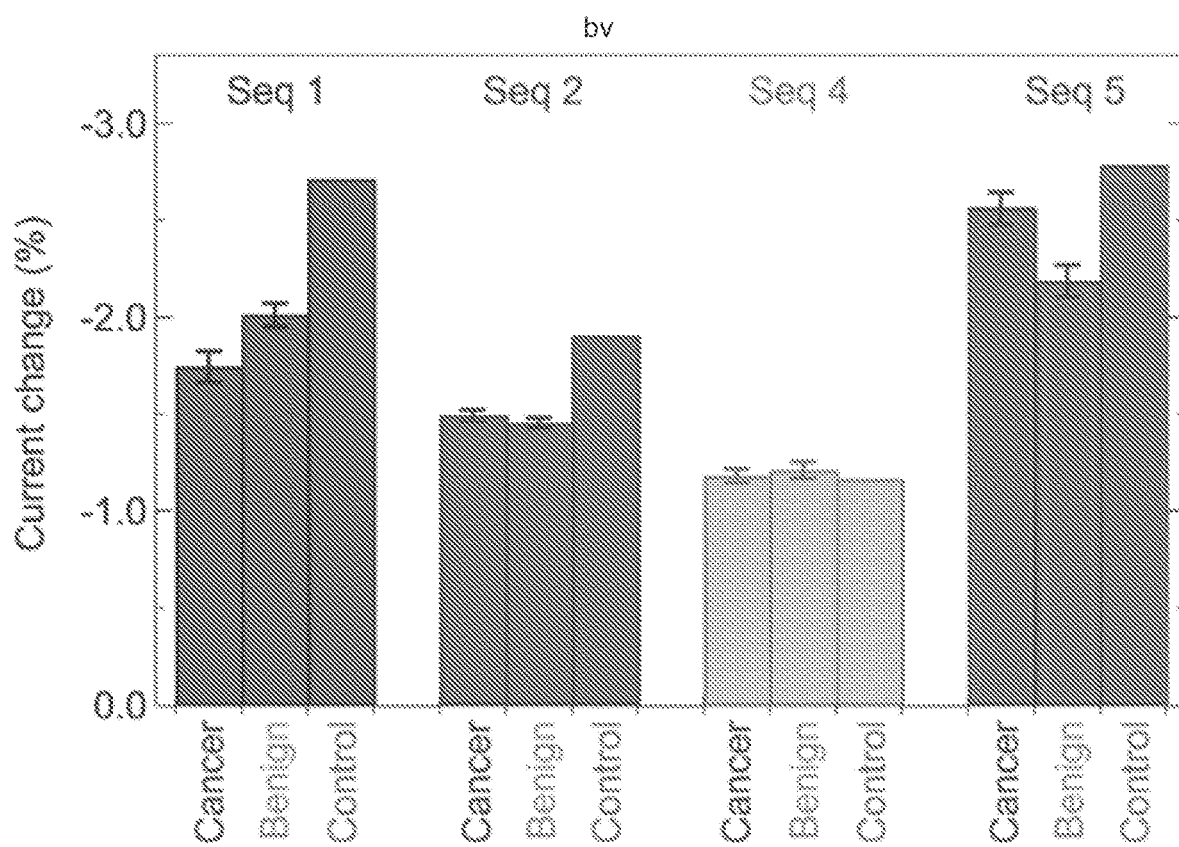
FIG. 6. Responses induced by the three serum headspace vapors for DNA-NT based on 4 different base sequences tested. Between 18 and 25 sensors of each type were used (error bars are derived as explained elsewhere herein).

FIG. 6 is a summary of sensor responses for the four sequences tested. One analysis would be to determine the average response across all devices and its uncertainty for each plasma type. In some cases, an individual device that responded more strongly than the average to one particular serum vapor was also likely to respond more strongly to the other serums. One may account for this by normalizing all response magnitudes for each device to the average response of that particular device to vapor from the control serum. These ratios are then averaged across all devices based on a particular DNA sequence. Finally, the ratios and their uncertainties are multiplied by the average control serum vapor response magnitude to retain the units of 'percent current change.'

The four sequences tested all show different overall response characteristics to the samples tested. DNA-NT based on Seq4 are unable to differentiate among the serum samples. Devices based on Seq2 differentiate between vapors from serum from patients with tumors (cancerous or benign) and serum from the healthy controls, but there is no distinction between the samples from patients with tumors. Devices based on both Seq 1 and Seq 5 are able to distinguish all three serum types. However, while devices based on Seq 1 respond more strongly to the benign serum than the cancer serum, the opposite is true for sequence 4. Without being bound to any particular theory, this is not unexpected, given that the electrical response of DNA-NT depends on the complex interaction between the complex VOC mixture from the headspace vapor and the binding sites on the sensor, which depend upon the DNA base sequence.

Thus, present here is a screening technology for ovarian cancer based on electronic detection and differentiation of vapors from serum samples. Vapors from pooled serum from women with ovarian tumors induced a clearly different response in DNA-coated carbon nanotube sensors than vapors from serum from healthy women. Moreover, the sensors were able to distinguish between pooled serum from women with benign tumors and pooled serum from donors with malignant tumors.

Screening analysis can be performed in minutes and the sensors are even reusable due to the non-covalent, short-lived attachment of the volatile molecules in the serum headspace to the sensor's DNA coating. Sensors are fabricated using scalable techniques that would be economically attractive. Further studies using serum samples from individual donors may be used to assess the variation between individuals that comprise each pooled group.

Definitions of exemplary, non-limiting DNA base sequences:

```
                                          (SEQ ID NO: 1)
Seq1-5' GAG TCT GTG GAG GAG GTA GTC 3'

(SEQ ID NO: 2)
Seq2-5' CTT CTG TCT TGA TGT TTG TCA AAC 3'
```

-continued

Seq4-5' CCC GTT GGT ATG GGA GTT GAG TGC 3' (SEQ ID NO: 3)

Seq5-5' GTA CGG ACT GTG AAT GCG CGT TAG 3' (SEQ ID NO: 4)

Additional Description

The following is additional supporting (but non-limiting) disclosure. As presented elsewhere herein, presented here is, inter alia, exploitation of volatile metabolites that may serve as biomarkers of the disease. Small organic compounds that possess vapor pressures at body and/or ambient temperatures give rise to odors (e.g., VOCs), and these compounds may be used as disease markers.

Translation of these biomarkers into functional diagnostic indicators that a physician can use in a clinical setting is one object of the present disclosure. One may use single walled carbon nanotube field effect transistors (FET's) functionalized with single stranded DNA (ssDNACNT) or other detection moieties, and examine the change in source drain current when exposed to VOCs. By varying the sequence of the adsorbed ss-DNA, the response of the ssDNACNT system can be tuned for desired sensitivity and specificity. The disclosed sensor class has a unique set of properties making them ideal for use in sensor arrays as part of what can be termed a "nanotechnology-enabled electronic nose" (NTE-nose) system.

It should be understood that a sensor can be constructed by testing various nucleotide sequences against various samples to determine which sequence or sequences yield a detectable signal when contacted with a particular analyte. For example, a user might generate three random 10-mer sequences and test those sequences against a disease sample and a well sample to see which of the sequences provides with the best way to distinguish between the two samples.

A sensor might thus contain five random 10-mer sequences, be calibrated against a control (well) sample, and then be calibrated against a disease sample so as to determine which of the sequences provided the greatest difference in signal when contacted with the two different samples. In this way, a user may construct a "library" of sequences and categorize the sequences by their sensitivity to particular samples. Similarly, a user might categorize sequences by their sensitivity to various VOCs so as to arrive at a library organized by the ability of its members to detect certain VOCs. Likewise, a user may generate a library of signals related to the interactions of various VOCs with various detector moieties (e.g., different polynucleotides)—once that library is generated, a user may then contact a given detector moiety to a sample (with one or more unknown VOCs) so as to generate a signal that is then compared against the signal library. The user may then determine which library signal most closely matches the sample signal, thus allowing the user to identify the VOC in the sample.

A user might also then compare a sequence's sensitivity to a particular VOC to the VOCs evolved from a particular disease sample so as to arrive at a sequence or set of sequences that are particularly suited to detect VOCs evolved from a particular sample and hence to determine the underlying condition of the patient that provided the sample from which those VOCs evolved.

A user may determine a "panel" that includes a set of detection moieties (e.g., three polynucleotides of different sequence) that is used to assay for the presence of one or more VOCs. In this way, a user may assemble a sensor that includes one, two, or more panels, and in this way a user may construct a custom device that includes panels of detection moieties so as to enable the device to detect the disease states (or VOCs) of interest to the user. Alternatively, a user may assemble devices that are configured to detect a preselected set of one or more VOCs known to be characteristic of specific device states.

The sensors may exhibit rapid response and recovery (on the order of seconds, or faster), very low signal drift, and chemical responses that are controlled by the base sequence of the ssDNA, The large number of distinct sequences even for short oligomers ($>10^{12}$ for strands of 20 bases) makes it possible to generate hundreds of sensors with uncorrelated odor responses as required for an e-nose with computational power approaching that of mammalian olfactory systems. The CNT FET functions as an array-able electronic readout element that is sensitive to variations in the electrostatic environment.

ssDNA may be chosen for functionalization of the CNTs because it displays recognition for VOCs, and the ssDNA may, in some embodiments, bind via a non-covalent $\pi$-$\pi$ stacking interaction to the CNT; this interaction preserves the latter's electronic readout properties. These sensors are capable of differentiating not only homologous series of compounds (aldehydes, carboxylic acids) but also structural and optical isomers, such as discriminating enantiomers of ($\pm$)-limonene. Although these compounds are all distinguishable by the human sense of smell, discrimination at the single carbon atom level by artificial electronic based sensors has been virtually unexplored. The present disclosure provides compelling evidence that a system with ssDNACNT sensors provides a powerful and functional electronic olfactory system that can be used to detect the presence of ovarian cancers, resulting in early detection and better prognoses.

Without being bound to any single theory, one might hypothesize that the endogenous volatile metabolites emanating from ovarian tissue would change with the onset of cancer-related metabolism. VOCs emanating from cancer, e.g., ovarian carcinoma, are thus a yet-untapped source of information regarding its presence.

Methods

Analytical-Organic Chemistry Techniques: VOCs may be collected, separated and analyzed using SPME and Gas Chromatography/Mass Spectrometry (GC/MS). SPME is a technology (Supelco Inc., Bellefonte, Pa.) that employs a thin fused-silica fiber coated with an adsorbent. The materials used for collection of all VOCs are the 2 cm, 50/30 µm Divinylbenzene/-Carboxen/polydimethylsiloxan (DVB/Carboxen/PDMS) "Stableflex" fibers (Supelco Corp.). VOCs evolving from a solid or liquid surface are exposed to the coated fiber and dissolve or absorb in the coating.

Cell cultures have been demonstrated to contain a complex mixture of components; consequently, SPME collections generate a wide variety of volatile components. GC/MS provides both qualitative and quantitative structural information of hundreds of components for a given sample.

Examination of Ovarian Cell lines. OVCAR3 cells were obtained along with two normal ovarian cell lines from the Ovarian Tissue Bank, University of British Columbia.

Cell Cultures: Each of the described cell lines were grown in duplicate. OVCAR 3 were maintained in RPMI 1640 supplemented with 10% fetal bovine serum and 100 µg/ml streptomycin, 100 units/ml penicillin. Cells were grown at 37° C. in a humidified atmosphere of 5% $CO_2$ in air. Normal ovarian cells, viz., IOSE 385 and HOSE 120, were obtained from the Canadian Ovarian Tissue Bank, Vancouver, Canada. They were cultured in a 1:1 combination of medium 199 (Sigma M5017) and MCDB 105 (Sigma M6395) containing 5% FBS and 50 µg/ml gentamicin in a humidified atmosphere of 5% $CO_2$-95% air. Cells were sub-cultured with 0.06% trypsin (1:250)/0.01% EDTA in $Mg^{2+}/Ca^{2+}$-free HBSS when confluent. Cells initially were maintained in plastic "T25" plates containing 4 ml of appropriate medium and were incubated at 37° C. in a humidified environment containing 5% $CO_2$. Media were changed 2 times a week and cells harvested once a week. The supernatants were taken from the culture media containing cells that had reached high confluence (≥100,000 cells/ml).

VOCs Emitted by Ovarian Cell Cultures: SPME was used to collect VOCs; VOCs were then desorbed, separated and analyzed by GC/MS.

Collection of VOCs from cell culture supernatants: Each cell line was grown in duplicate. The supernatants (~5 ml each) were taken from the culture media containing cells that had reached high confluence (≥100,000 cells/ml) One milliliter of supernatant was used for each analysis and the remainder was frozen at −20° C. for future use. In addition to harvesting the cell-free supernatants to examine VOCs released into these media, comparable volumes (one ml) of the specific growth media used for each cell type were also obtained.

Volatile biomarkers of ovarian carcinoma are present and may be detected in vaginal secretions. Vaginal secretions in normal, healthy women have pH's between 4-5. Initially examined were the volatiles emitted by acidified supernatants from all cell types as well as media for cell growth. The VOCs from each supernatant were collected by solid-phase microextraction (SPME). This procedure involves adding 1 ml of supernatant to a 4 ml vial with a 7 mm×2 mm Fisherbrand® micro stirring bar and 750 mg of NaCl. The vial was capped with a silicone/TFE septa cap and was placed in a water bath equilibrated at 37° C. while being stirred for 30 minutes. A 2 cm, 50/30 µm Divinylbenzene/Carboxen/Polydimethylsiloxane (DVB/Carboxen/PDMS) "Stableflex" SPME fiber (Supelco Inc., Bellefonte, Pa.) was exposed to the supernatant headspace for 30 minutes. The fiber with extracted VOCs was then transferred to the GC/MS for desorption, separation, and analysis. Hydrochloric acid and sodium hydroxide were used to adjust the pHs. To examine intra-sample variations, each cell type was cultured in three separate batches and two of the batches from each cell type were analyzed.

Gas chromatography/mass spectrometry (GC/MS): A Thermo-Finnigan Trace GC/MS (Thermo Electron, San Jose, Calif.) system was used. The Trace GC/MS was equipped with a Stabilwax column (30 M×0.32 mm with 1.0µ coating; Restek, Bellefonte, Pa.) which was used for separation and analysis of the desorbed volatiles. The following chromatographic protocol was employed for separation before MS analyses: 60° C. for 4 min, then programmed at 6° C./min to 210° C. with a 20-min hold at this final temperature. Column flow was constant at 1.5 ml/min. The injection port was held at 230° C. Operating parameters for the mass spectrometer were as follows: ion source temperature, 200° C., ionizing energy at 70 eV; scanning frequency was 4/s from m/z 41 to m/z 300.

Data Analysis: Compounds found in each total ion chromatogram (TIC) are separately normalized in the following manner: one may examine the mass spectra of all peaks ~1% above baseline to eliminate components arising from siloxanes, room air, fragrances, cosmetics, soaps, solvents, e.g., traces of chloroform, column and septa, and solvents commonly employed in cosmetic room air products, e.g., 2-butoxy ethanol. The intensities of remaining components are normalized by dividing each of their intensities by the sum of all intensities for remaining compounds. This transformation is comparable to other normalization methods used in GC/MS data analysis which generally normalize to the total intensity, e.g., by dividing extracted peak intensity values by the sum of intensity values for the chromatogram.

38 compounds were chosen for quantitative comparison. The compounds examined were present in both types of cell growth media; as well as both cell types. Cancer cells can markedly alter the production of media-related VOCs through up-take and metabolism. The resulting data (normalized areas) were subjected to 6 multivariate analyses of variance with SPSS (version 16). In some analyses, one may consider only p values of 0.001 or less as significantly different.

Results

VOCs Emitted by Ovarian Cell Cultures: In addition to harvesting the cell-free supernatants to examine VOCs released into these media, one may also examine comparable volumes (1 ml) of the specific growth media used for each cell type. T25 containers can be sources of many plastic-related VOCs. Consequently, media or the cell-free supernatants are employed for the analyses. Vaginal secretions in normal, healthy women have pH's between 4-5. Initially examined were the volatiles emitted by acidified supernatants from all cell types as well as media for cell growth. SPME was used to collect VOCs, which were then desorbed, separated and analyzed by GC/MS. Many compounds in the complex mixture of VOCs above the samples were eliminated from quantitative analyses because they were easily recognized contaminants. 38 compounds were chosen for quantitative comparison. The compounds examined were present in both types of cell growth media; as well as both cell types. Duplicate analyses were performed on each cell line and growth media. The resulting data (normalized areas) were subjected to 6 multivariate analyses of variance with SPSS (version 16). Again, one may consider only p values of 0.001 or less as significantly different.

Adapting these conservative numbers, it was found that VOCs emanating from the OVCAR3 cell lines are quantitatively very distant from those obtained from normal cell lines (F=803; p=0.000004). In contrast, the VOCs emanating from the media for each cell type are quantitatively, similar (F=3.39; p=0.132).

Figure 7A:
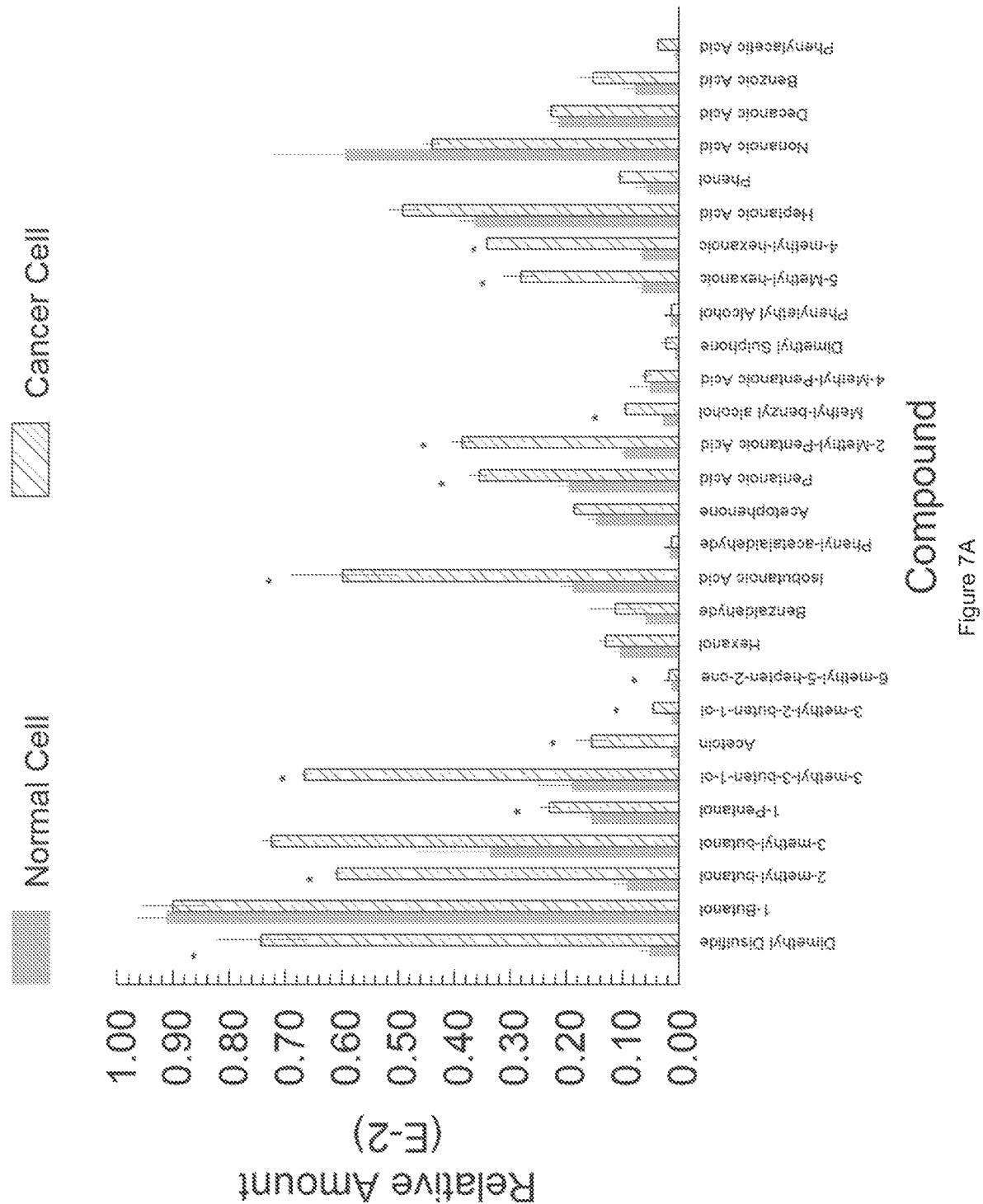

These results are depicted in FIGS. 7a and 7b, which demonstrates the preponderance of significantly higher VOCs from the OVCAR3 cells. Only acetic acid and isovaleric acid are present in greater relative amounts in normal cell supernatant than in cancer cell supernatant. Acetic acid was present in greater relative amounts in the normal cell media. However, the remaining differences are not due to differences in the media used to grow the cells; they are the result of the differences in cellular metabolic processes.

Power Analyses: Concomitant with the mutivariate analysis of variance, also examined were the power estimates for each compound analyzed. As described above, a large numbers of compounds clearly distinguish disease from normal in these cell systems. The power estimates for these compounds range from 0.984 to 1.000. Increasing samples size may strengthen the discrimination between disease and normal.

Reproducibility of analyses: Also examined was the test-retest reliability of our analytical methods during examination of ovarian cells and found the reliability to be excellent. Reliability, i.e., reproducibility, for the majority of all normalized peak areas were >0.90.

Figure 8:
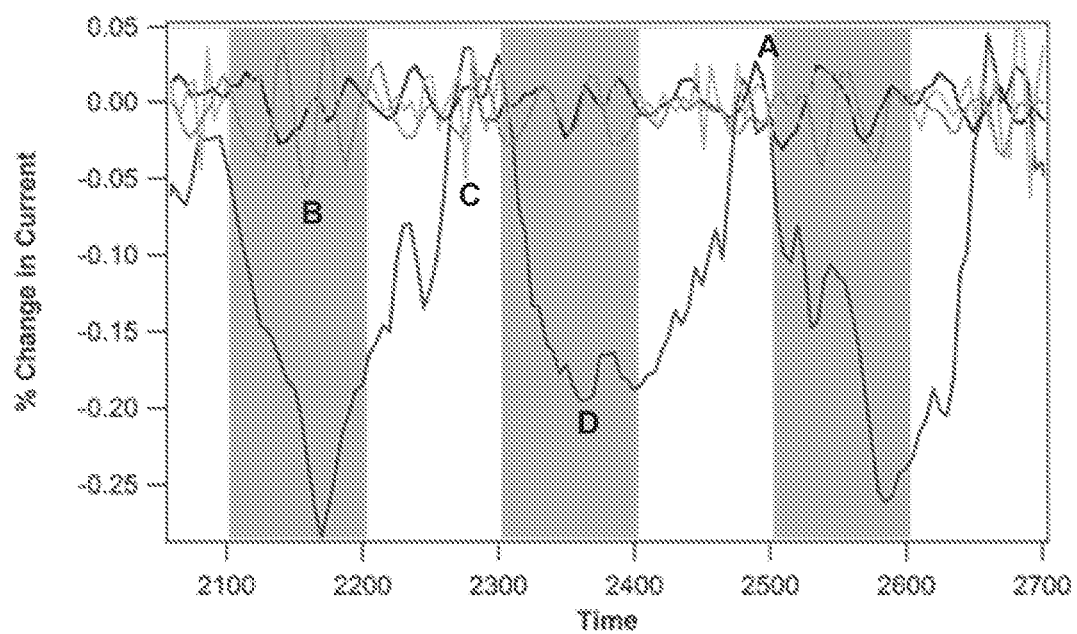
FIG. 8: DNA-NT sensor discriminates VOCs emanating from supernatants containing metabolites of in vitro cell systems. The signal associated with normal ovarian cells is at the noise level (data A). The media in which normal ovarian cells were grown also yielded a small signal (data B). In addition, the media in which cancerous, OVCAR3 cells were grown yields a very small signal (data C). In contrast, the supernatant from a sample of cancerous ovarian cells yields a large, reproducible signal (data D).

Response of single stranded DNA coated nanotubes (ssDNACNT) to Supernatants from Ovarian Cell Cultures: Employed was a single ssDNACNT vapor sensor to examine and discriminate the VOCs emanating from the in vitro ovarian cell systems. Employed was ssDNA "sequence 2-alpha" (aaaaccccggggtttttttttt (SEQ ID NO: 5)) to examine the supernatants containing metabolites from normal ovarian cells, OVCAR3 cancer cells and the growth media used for each. FIG. 8 demonstrates that the sensor can clearly discriminate cancer cell emanations from normal cells and the media used to grow cells. The test-retest reliability of the ssDNACNT sensor measurements was also determined with two, one ml aliquots of the same supernatants and found to be excellent with a 0.97 correlation between duplicate analyses.

The data reveal marked differences between normal ovarian cells and commonly encountered types of cancer cells. In addition, one may also note that OVCAR3 and normal ovarian cells appear to metabolize leucine and isoleucine differently, which is suggested by the different relative amounts of isovaleric acid and 2-methylbutyric acid, respectively. Cancer cells produce much greater relative amounts of the 2-methyl acid than normal ovarian cells. Further many of the VOC differentiating cancer from normal are acidic compounds, which may be easily identified and quantified in human vaginal secretions. These acids may be identifiable in vaginal secretions which will allow one to infer abnormal changes deeper in the reproductive tract.

Additional Illustrative Results

The odorant signature of ovarian cancer in pooled plasma samples was confirmed using three approaches: DNA-NT sensor arrays, analytical chemistry, and trained detection dogs.

The odorant signature of ovarian cancer and the VOCs that constitute this signature were examined using plasma samples collected from ovarian cancer patients, patients with benign ovarian growths, and age-matched, healthy controls. Initial measurements were conducted on pooled samples (n=10 for each class of subjects). Analyzing pools allowed observation of what may be average amounts of VOCs in each category of patients and controls as well as obvious differences attributed to subject status. Measurements of pooled plasma samples from the three populations provided strong evidence that their odorant profiles can be differentiated using the three complementary techniques.

DNA-NT sensor measurements were based on arrays consisting of 10 different device types with 10 realizations each, for a total of 100 DNA-NT sensors. Sensor response was reported as average percent change in the current across the set of identically prepared DNA-NT, since it is shown that this compensates effectively for sample-to-sample resistance variations.

As set forth elsewhere herein, experiments were first conducted with DNA-NT sensors based on four different random oligomers that showed performance in earlier experiments:

```
                                            (SEQ ID NO: 1)
Seq1-5' GAG TCT GTG GAG GAG GTA GTC 3'

(SEQ ID NO: 2)
Seq2-5' CTT CTG TCT TGA TGT TTG TCA AAC 3'
```

```
                                            (SEQ ID NO: 3)
Seq4-5' CCC GTT GGT ATG GGA GTT GAG TGC 3'

(SEQ ID NO: 4)
Seq5-5' GTA CGG ACT GTG AAT GCG CGT TAG 3'.
```

DNA-NT sensors based on Seq1 showed clear differential responses to the headspace vapor from the various pooled samples (FIGS. 5 and 6). As seen in the summary plots of FIG. 6, the other sequences led to DNA-NT sensors that showed a differential response to the control pool (Seq2), the benign tumor pool (Seq5), and no observed discrimination power (Seq4). This diverse set of responses is further evidence that the disclosed systems function as electronic olfaction systems for detecting an odor signature of various cancers, e.g., ovarian cancer.

SPME-GC/MS is a sensitive analytical method to collect, separate and identify the VOC signature and its individual components that distinguish patients with ovarian cancer from controls. It was found that pooled plasma samples from the three subject groups are qualitatively similar in their major components but also differ quantitatively in VOC profiles.

Figure 9A:
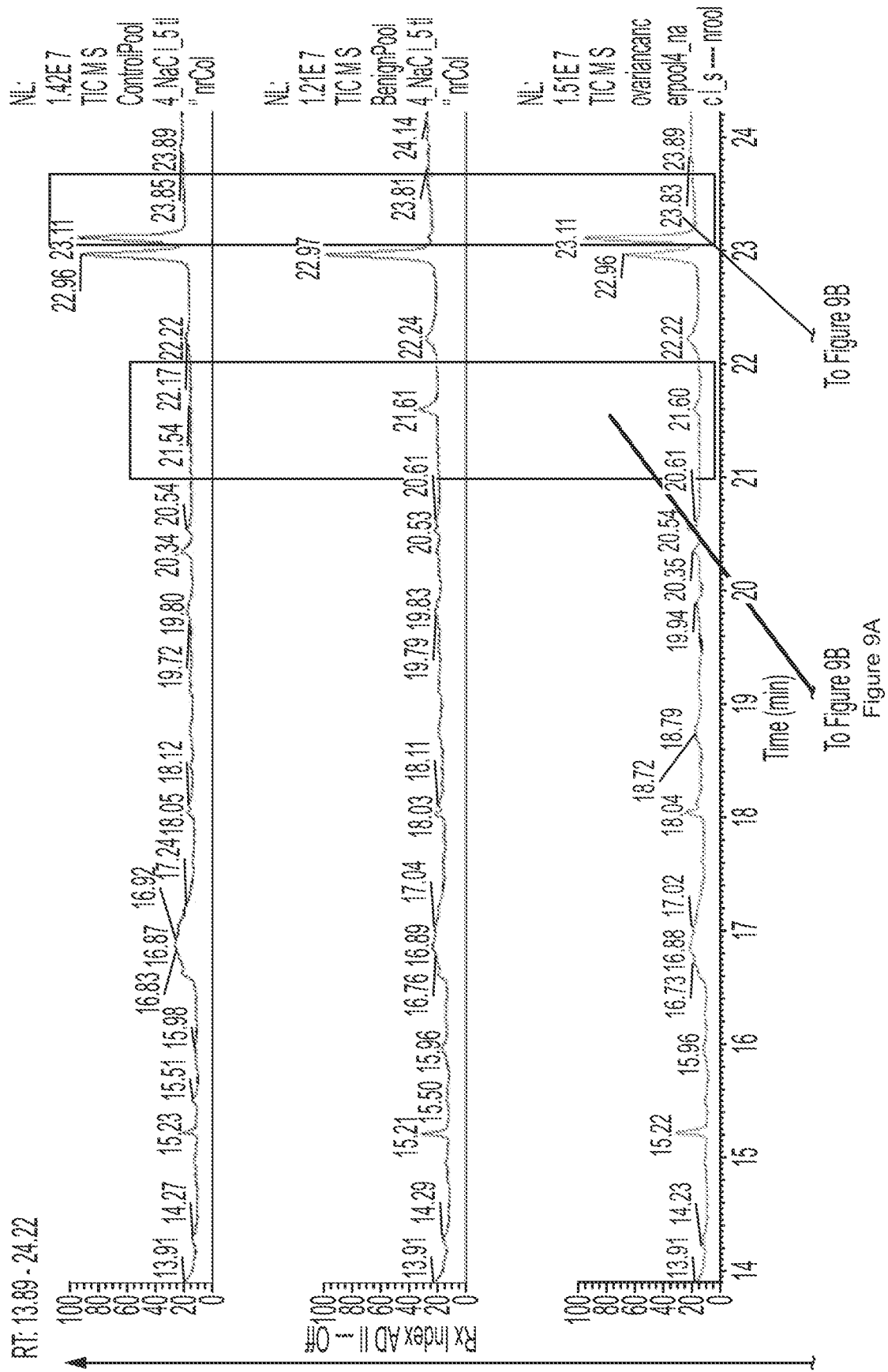
FIG. 9. Analysis of Pooled Samples by GC/MS The top three plots show differences in selected regions in the Total Ion Chromatographs obtained from analyses of SPME-collected VOCs from the three pooled samples (top: control group; middle: benign tumor group; bottom: ovarian cancer group). The bottom two plots show the mass spectrometry data for the two compounds that show the strongest differences. These have been identified as 3,4-dimethylbenzaldehyde (top mass spectrum) and dimethylsulfone (bottom mass spectrum).
Figure 9B:
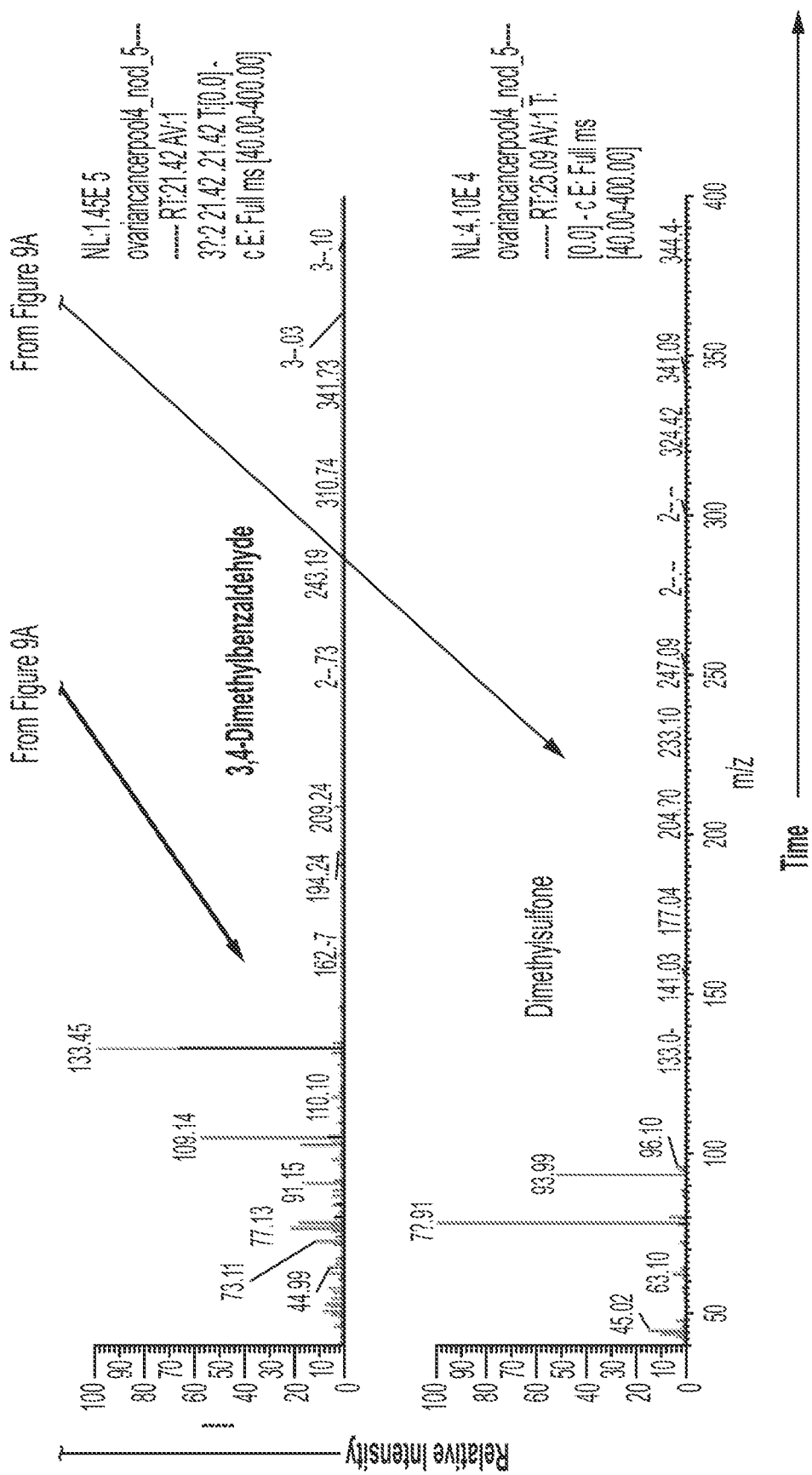

As one example, FIG. 9 shows that dimethylsulfone, a commonly occurring mammalian metabolite of methionine, differs among groups, with the largest amounts of the metanolite being present in the controls (top Total Ion Chromatograph or TIC) and cancer patients (bottom TIC). The large component eluting prior to dimethylsulfone is butylated hydroxytolune (commonly referred to as BHT). BHT is an exogenous compound that may be found in analysis of the vacutainer tubes used for blood collection.

Another possible difference in the three groups appears to be 3,4-dimethylbenzaldehyde, which elutes at a retention time of approx. 21.60 minutes. Without being bound to any particular theory, an initial examination of the relative amounts of the 3,4-dimethybenzaldehyde in the pooled samples suggests that the compound is present in highest amounts in samples from people with benign growths, less in those with ovarian cancer and almost none in healthy controls.

Figure 10:
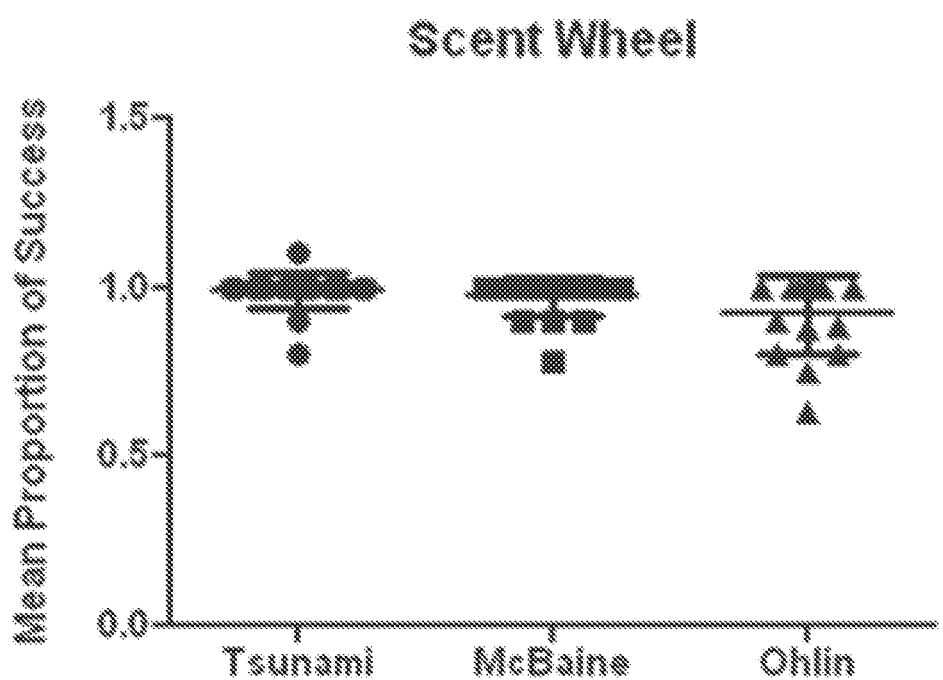
FIG. 10. Success of canine biosensing of ovarian cancer. Dogs were exposed to 50 uL of plasma pooled from 10 ovarian cancer patients (true positive), 10 patients with benign ovarian disease and 10 age matched controls. Mean proportion of success =number of correct trials/total number of trials.

Results from an exemplary cohort of trained canines are consistent with earlier reports on dogs trained to detect cancer in ovarian tissue as well as blood samples. Experiments indicate the presence of an odor signature in blood plasma, with a >90% success rate (# of correct trials/total number of trials) for canine detection of pooled plasma samples from ovarian cancer patients over pooled samples from healthy controls (n=10 for each). In addition, dogs moved onto discriminating plasma samples from both patient groups and healthy controls: all three dogs are at 90% or better mean proportion of success (FIG. 10). Once trained to recognize the ovarian cancer odors, the dogs are able to analyze the signals and ignore confounding outside stimuli; dogs may thus be used (e.g., trained) to validate candidate molecules for VOC sensors.

Using three approaches to detect the odor signature of ovarian cancer is detected in plasma samples from individual patients.

Measurements of individual samples from which the pooled samples were made, were also conducted to determine the pattern of VOCs across the three groups of samples. The results of the canine study were presented above and also in FIG. 10. GC/MS data were manually culled to eliminate exogenous compounds, and 24 compounds whose structures suggested their origin as human metabolites were examined across all patients and controls.

Figure 11:
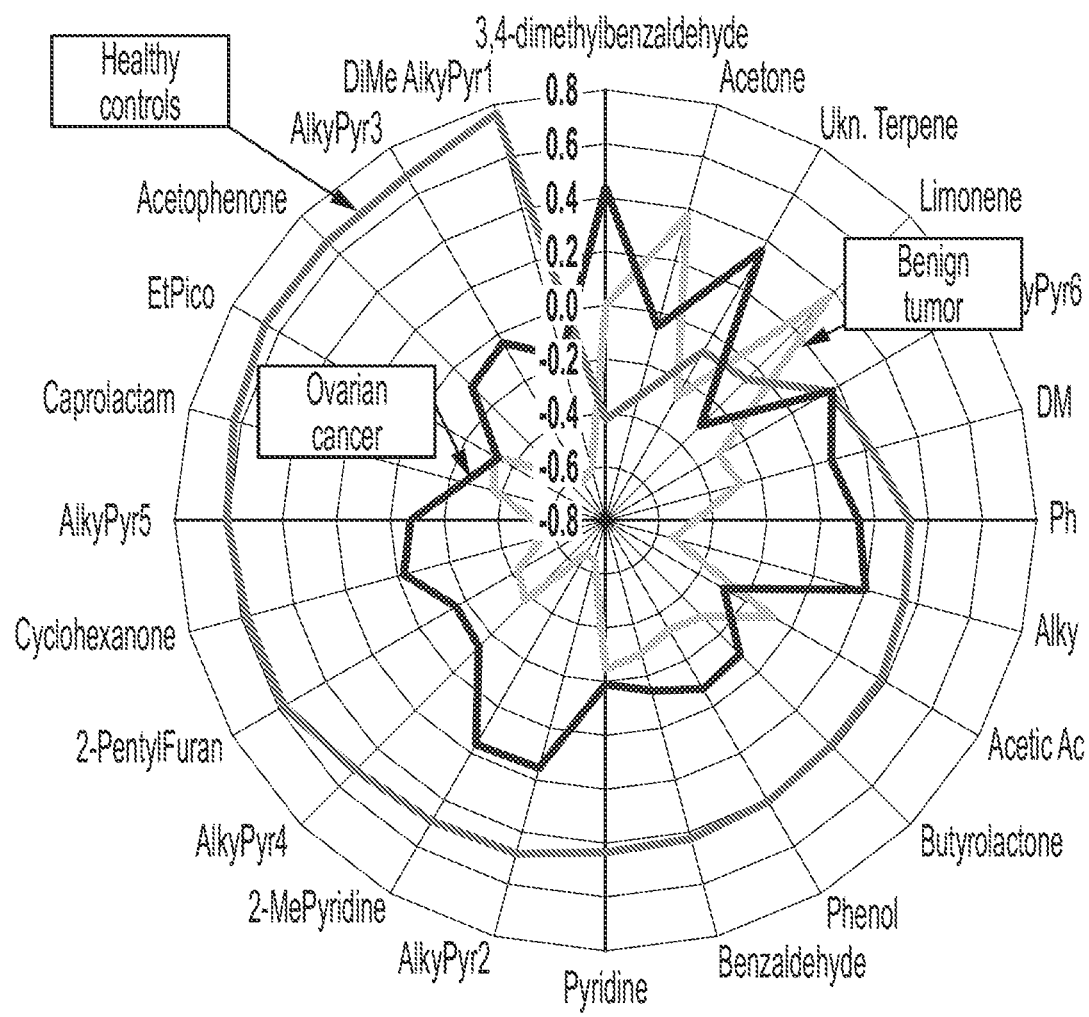
FIG. 11. "Radar plot" comparing the VOC profile of the three subject groups; healthy controls; ovarian cancer; and benign tumors. The z-transformed data show significant differences among the three groups.

The relative amounts of these 24 compounds were calculated in all samples. To better visualize the relationships across groups, z-transformed values corresponding to the relative amounts of the 24 VOCs were used to create a "radar plot" (FIG. 11). Z-transforms within compounds were chosen so the data could be plotted on the same axis. This figure clearly shows that with the exception of only four VOCs, normal controls produce higher relative amounts of the VOCs than either primary cancer patients or those with benign, non-cancerous growths.

A second analysis methodology was developed. The method was designed to be robust for small sample sizes, which is not the case for many statistical techniques commonly applied to large-dimensional samples (e.g. Linear Discriminant Analysis). The SPME GC/MS output for each individual is a vector in a 24-dimensional space, with one dimension for each VOC.

Figure 12:
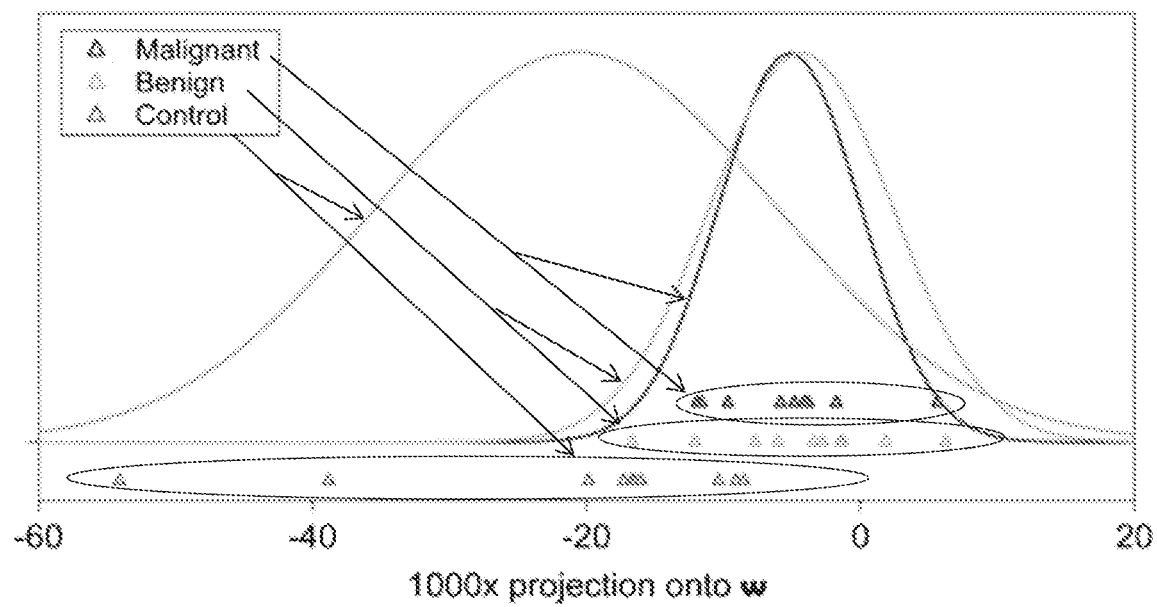
FIG. 12. Visualzation of GC/MS data from individual plasma samples. The vector representing VOCs for each subject, as determined by SPME-GC/MS, is projected along the vector connecting the average response of healthy controls and that of patients with malignant cancer. Triangles along the x-axis correspond to each sample tested. The data points from the malignant, benign and control classes are offset vertically to avoid obscuring data. Gaussian curves are estimated distributions of each group, based on the mean and standard deviation. The distributions associated with malignant and benign tumors are clearly distinguished from that of the healthy controls, as indicated by the p-values of 0.0042 and 0.0033, respectively.

To account for samples that were excessively concentrated or too weak (no internal standards were used) ony may normalize the size of the responses using a "$L_1$ normalization"[5] and then calculate the 24-dimensional vector in "VOC space" corresponding to the average relative amounts of each VOC for each patient class. One may define the (vector) difference between the average vectors of the malignant and control groups, which corresponds to the "direction" in VOC space that best separates the patients with malignant tumors from controls. One may then take the projection of each individual vector along and $\vec{w}$ visualize the results by plotting along the number line (FIG. 12) where the x-axis represents position along the direction $\vec{w}$. For clarity, the data points from the three sets are offset vertically.

While there is overlap between the control and malignant data points, the distributions look clearly different. In addition, one may estimate Gaussian fits to the data, based on their mean and standard deviation.

The data format is appropriate for a single Welch's t-test to compare two data sets and evaluate the probability of the null hypothesis that the mean values for the sets are equal. With no assumptions as to the variances of the control and malignant data, one finds p=0.0042 for these two data sets. Similarly, the benign and control data are significantly different distributions, with p=0.0033. One may note that a p value less than 0.01 is typically taken as strong evidence that the mean values for the sets are distinct.

Figure 13:
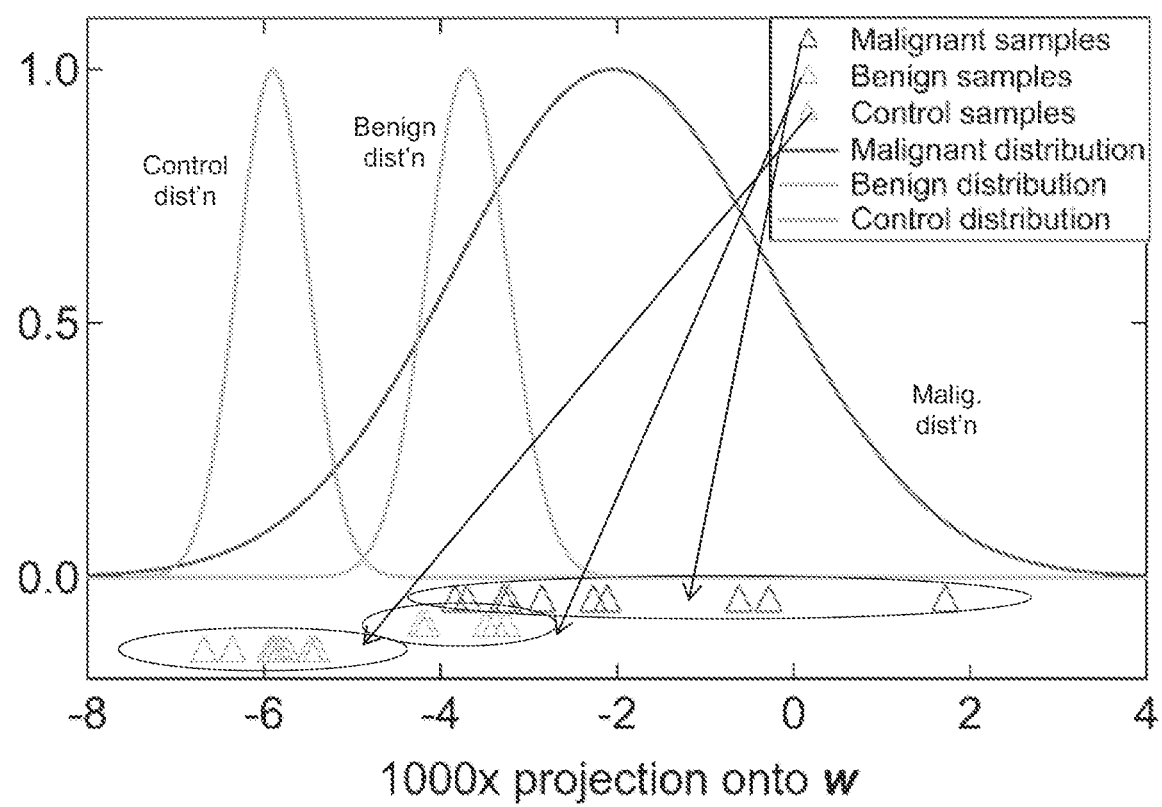
FIG. 13: Visualization of DNA-NT sensor data from individual plasma samples. The response vector for each subject is projected along the vector connecting the average response of healthy controls and that of patients with malignant cancer. Triangles along the x-axis of the plot correspond to each sample tested. Vertical offsets of malignant, benign and control classes are to avoid obscuring data. Control data are highly clustered and show minimal overlap with the malignant and benign sets. Gaussian curves are estimated distributions of each group, based on the mean and standard deviation. malignant and benign tumors are clearly distinguished from that of the healthy controls, as indicated by the p-values of $3\times10^{-5}$ and $6\times10^{-5}$, respectively.

Individual samples were also analyzed using 142 DNA-NT sensors based on 10 different DNA oligomers (oligomer sequences known, but not listed so as to save space). The data show individual variation within each group, and the data agree qualitatively with results from pooled samples (FIGS. 5, 6). Using the statistical method described in the preceding paragraph for GC/MS data, the DNA-NT sensor response data were analyzed in the 10-dimensional "sensor space" and projected onto the $\vec{w}$ direction (FIG. 13). The data format is again appropriate for a single tail Welch's t-test to evaluate the probability of the null hypothesis (equal mean values for the sets). The analysis indicates that combining the information from responses across the full set of ten sensor types significantly enhances the power of the approach. The p-values for the projections onto the difference vector were $\sim 6 \times 10^{-5}$ for the control-malignant pair, $3 \times 10^{-5}$ for control-benign, and 0.02 for benign-malignant. This result is achieved using 10 randomly selected DNA sequences with no screening for effectiveness. This further demonstrates that the disclosed sensors are a powerful diagnostic. In some, These data demonstrate that the signature of ovarian cancer is detected in plasma samples from individual patients using each of the three approaches.

Additional device information is provided in FIG. 14, which figure provides information about an exemplary device. A set of exemplary CNT FET arrays was based on high purity (98%) semiconducting CNTs, deposited from a suspended solution (NanoIntegris Inc.). The substrate consisted of $Si/SiO_2$ wafers onto which a 20 nm thick layer of aluminum oxide ($Al_2O_3$) was deposited via atomic layer deposition (ALD) to promote CNT-surface adhesion. Cr/Au electrodes were defined using standard photolithography techniques and a sparse network of CNTs was deposited from solution by drop-casting onto the electrode arrays.

Figure 14A:
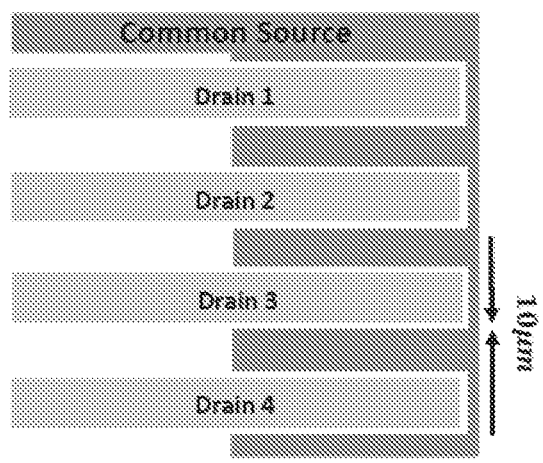
FIGS. 14A-14C (DNA-NT Nanosensor Array).
Figure 14B:
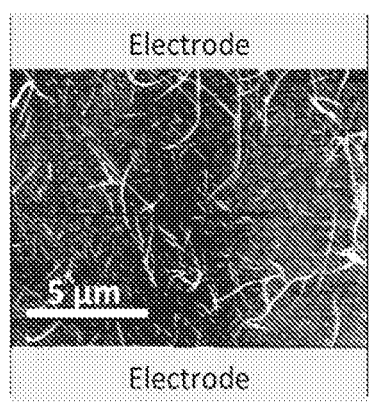
Figure 14C:
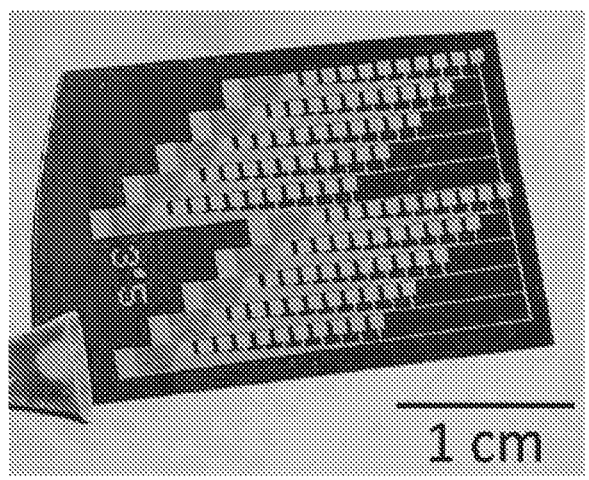

The electrode design used individual source fingers, interdigitated with a common drain electrode (FIG. 14a). The effective device area of 10 μm×2 mm ensured that, even for a sparse network, many CNTs spanned each electrode pair, leading to a suitable device yield (e.g., over 90%) and also good reproducibility of device properties (FIG. 14b). Additionally, the drain electrodes were sufficiently separated such that no undesired shorting paths were created. Each FET array contained 100 devices, arranged as ten sets of ten devices. Each set may be addressed independently for functionalization with a specific DNA oligomer, and each device has its own contact pads such that all 100 device responses can be recorded individually (FIG. 14c).

CNTs were then functionalized with single stranded DNA (ssDNA) sequences ranging from 21 to 24 base pairs in length by pipetting microliter droplets of 100 μM DNA solution onto the devices and allowing the DNA strands to diffuse to and bind onto the sidewalls of the CNTs. After 30 minutes, compressed nitrogen was used to remove the solution and unbound DNA strands, leaving a monolayer coating of ssDNA strands non-covalently bound to the carbon nanotubes via π-π stacking.

What is claimed:

1. A detection device, comprising:
   a substrate having a surface;
   a semiconductor and a detection moiety in electronic communication with one another,
   the detection moiety comprising a polynucleotide that includes one or more of 5' CCC GTT GGT ATG GGA GTT GAG TGC 3' (SEQ ID NO: 3) and 5' GTA CGG ACT GTG AAT GCG CGT TAG 3' (SEQ ID NO: 4),
   the substrate supporting the semiconductor and the semiconductor being arranged substantially parallel to the surface of the substrate,
   the detection moiety being configured to detect one or more volatile organic compounds present in a biological sample; and
   a sensor chamber configured to retain therein the one or more volatile organic compounds present in the biological sample,
   the device being configured such that the detection moiety is capable of fluid communication with the interior of the sensor chamber.

2. The device of claim 1, wherein the semiconductor comprises graphene, a carbon nanotube, $MoS_2$, zinc oxide, $WS_2$, silicon germanium, gallium arsenide, indium phosphide, gallium nitride, or any combination thereof.

3. The device of claim 1, wherein the detection moiety comprises a polypeptide.

4. The device of claim 1, wherein the one or more volatile organic compounds comprises dimethylsulfone, 3,4-dimethyl benzaldehyde, an alkyl substituted pyridine, cyclohexanone, 2-pentylfuran, caprolactam, or any combination thereof.

5. The device of claim 1, wherein the device comprises a monitor configured to detect a signal, a change in signal, or both related to an interaction between the detection moiety and a volatile organic compound of a biological sample.

6. The device of claim 1, wherein the detection moiety is bound to the semiconductor by pi-pi orbital interaction.

7. The device of claim 1, wherein the device further comprises a heater configured to heat the interior of the sensor chamber.

8. The device of claim 1, wherein the device further comprises a source of salt configured for addition to the biological sample.

9. The device of claim 1, wherein the device comprises two electrodes and wherein the semiconductor is disposed in a conductive path that places the two electrodes into electronic communication with one another.

10. The device of claim 1, wherein the sensor chamber defines a headspace within, and wherein the detection moiety is disposed within the headspace.

11. The device of claim 1, further comprising a vacuum device configured to encourage release of one or more volatile organic compounds present in the biological sample.

12. A method, comprising:
(i) exposing a device comprising:
a semiconductor and a detection moiety in electronic communication with one another,
the detection moiety comprising a polynucleotide that includes one or more of 5' CCC GTT GGT ATG GGA GTT GAG TGC 3' (SEQ ID NO: 3) and 5' GTA CGG ACT GTG AAT GCG CGT TAG 3' (SEQ ID NO: 4),
the detection moiety being configured to detect one or more volatile organic compounds present in a biological sample, and
a sensor chamber,
the device being configured such that the detection moiety is capable of fluid communication with the interior of the sensor chamber,
to an atmosphere above a biological sample from a patient, the atmosphere comprising one or more volatile organic compounds of the sample; and
(ii) detecting a signal, a change in signal, or both related to exposing the device to the atmosphere.

13. The method of claim 12, further comprising adding a material to the biological sample that encourages one or more volatile organic compounds from the sample into the atmosphere, heating the biological sample, applying a reduced pressure to the biological sample, or any combination thereof.

14. The method of claim 13, wherein the material comprises a salt.

15. The method of claim 12, wherein the change in signal comprises a change in current, a change in voltage, a change in resistance, a change in intensity, a change in wavelength, or any combination thereof.

16. The method of claim 12, further comprising correlating the signal, the change in signal, or both, to a disease state of the patient.

17. The method of claim 16, wherein the disease state comprises cancer.

18. The method of claim 16, wherein the correlating comprises comparing the signal, change in signal, or both to a signal, a change in signal, or both to a standard.

19. The method of claim 18, wherein the standard comprises a well patient.

20. The method of claim 18, wherein the standard comprises a disease state patient.

* * * * *

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
gagtctgtgg aggaggtagt c                    21

```
<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cttctgtctt gatgtttgtc aaac                                          24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
cccgttggta tgggagttga gtgc                                          24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtacggactg tgaatgcgcg ttag                                          24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aaaacccccg gggtttttttt tttt                                         24
```